US011583344B2

(12) United States Patent
Hladio et al.

(10) Patent No.: US 11,583,344 B2
(45) Date of Patent: *Feb. 21, 2023

(54) DEVICES, SYSTEMS AND METHODS FOR NATURAL FEATURE TRACKING OF SURGICAL TOOLS AND OTHER OBJECTS

(71) Applicant: INTELLIJOINT SURGICAL INC., Kitchener (CA)

(72) Inventors: Andre Novomir Hladio, Waterloo (CA); Armen Garo Bakirtzian, Kitchener (CA); Richard Tyler Fanson, Stoney Creek (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 296 days.

This patent is subject to a terminal disclaimer.

(21) Appl. No.: 16/901,730

(22) Filed: Jun. 15, 2020

(65) Prior Publication Data

US 2020/0305986 A1   Oct. 1, 2020

Related U.S. Application Data

(63) Continuation of application No. 15/522,559, filed as application No. PCT/CA2015/000560 on Oct. 29, 2015, now Pat. No. 10,682,185.

(Continued)

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/6847* (2013.01); *A61B 17/1703* (2013.01);
(Continued)

(58) Field of Classification Search
CPC ......... A61B 34/10; A61B 34/20; A61B 30/06; A61B 2090/062; A61B 5/6847; A61B 5/6878

See application file for complete search history.

(56) References Cited

U.S. PATENT DOCUMENTS 5,288,785 A   2/1994   Jow et al.
5,978,167 A   11/1999  Abe
(Continued)

FOREIGN PATENT DOCUMENTS

CA   2826925 A1   8/2006
CA   2651782 A1   11/2007
(Continued)

OTHER PUBLICATIONS

Creaform; Portable 3D Scanners: Handyscan 3D; Apr. 16, 2016; 3 Pages; Web Link: www.creaform3d.com/en/metrology-solution/portable-3d-scanner-handyscan-3d.
(Continued)

*Primary Examiner* — Matthew J Lawson

(57) ABSTRACT

Systems, methods and devices for use in tracking are described, using optical modalities to detect spatial attributes or natural features of objects, such as, tools and patient anatomy. Spatial attributes or natural features may be known or may be detected by the tracking system. The system, methods and devices can further be used to verify a calibration of a tool either by a computing unit or by a user. Further, the disclosure relates to detection of spatial attributes, including depth information, of the anatomy for purposes of registration or to create a 3D surface profile of the anatomy.

18 Claims, 20 Drawing Sheets

Related U.S. Application Data

(60) Provisional application No. 62/084,891, filed on Nov. 26, 2014, provisional application No. 62/072,041, filed on Oct. 29, 2014, provisional application No. 62/072,032, filed on Oct. 29, 2014, provisional application No. 62/072,030, filed on Oct. 29, 2014.

(51) Int. Cl.
| | | |
|---|---|---|
| *A61B 34/10* | (2016.01) | |
| *G06T 7/73* | (2017.01) | |
| *G06T 7/33* | (2017.01) | |
| *A61B 46/10* | (2016.01) | |
| *A61B 90/30* | (2016.01) | |
| *A61B 90/00* | (2016.01) | |
| *A61B 17/17* | (2006.01) | |

(52) U.S. Cl.
CPC ............. *A61B 34/10* (2016.02); *A61B 46/10* (2016.02); *A61B 90/06* (2016.02); *A61B 90/30* (2016.02); *A61B 90/361* (2016.02); *G06T 7/337* (2017.01); *G06T 7/74* (2017.01); *A61B 2034/105* (2016.02); *A61B 2034/2048* (2016.02); *A61B 2034/2055* (2016.02); *A61B 2034/2057* (2016.02); *A61B 2034/2065* (2016.02); *A61B 2034/2068* (2016.02); *A61B 2034/2072* (2016.02); *A61B 2090/061* (2016.02); *A61B 2090/064* (2016.02); *A61B 2090/067* (2016.02); *A61B 2090/364* (2016.02); *A61B 2090/373* (2016.02); *A61B 2090/3937* (2016.02); *A61B 2090/3983* (2016.02); *G06T 2207/30008* (2013.01)

(56) References Cited

U.S. PATENT DOCUMENTS

| | | | | |
|---|---|---|---|---|
| 2004/0059216 | A1* | 3/2004 | Vetter | A61B 90/36 600/424 |
| 2007/0249967 | A1* | 10/2007 | Buly | A61B 5/1121 600/595 |
| 2009/0118613 | A1* | 5/2009 | Krugman | A61B 18/1206 600/407 |
| 2009/0143973 | A1* | 6/2009 | Litvin | A61B 34/20 600/407 |
| 2009/0259230 | A1* | 10/2009 | Khadem | A61B 34/20 128/898 |
| 2010/0305439 | A1* | 12/2010 | Shai | A61B 18/02 434/262 |
| 2012/0157887 | A1 | 6/2012 | Fanson et al. | |
| 2014/0275940 | A1 | 9/2014 | Hladio et al. | |
| 2014/0277555 | A1* | 9/2014 | Meridew | A61B 17/1742 623/22.12 |
| 2015/0157419 | A1* | 6/2015 | Bell | A61B 34/10 382/103 |
| 2015/0305823 | A1* | 10/2015 | Claus | A61B 34/20 600/424 |
| 2017/0296274 | A1* | 10/2017 | van der Walt | A61F 2/4609 |
| 2020/0022615 | A1* | 1/2020 | Schoepp | A61B 34/20 |

FOREIGN PATENT DOCUMENTS

| | | |
|---|---|---|
| CA | 2892554 A1 | 9/2014 |
| CA | 2907554 A1 | 9/2014 |
| CA | 2897873 A1 | 10/2014 |
| WO | 2013171338 A1 | 11/2013 |
| WO | 2014139019 A1 | 9/2014 |

OTHER PUBLICATIONS

International Search Report dated Jan. 12, 2016, Issued by the Canadian Intellectual Property Office for International PCT Patent Application No. PCT/CA2015/000560.
David W. Arathorn, Using the Map-Seeking Circuit Algorithm in Object Recognition, Article, May 2015; 7 Pages.
Claron Technology, Micron Tracker 3, Article, 2012, 8 Pages.
Brainlab, Surface Mathching With Z-Tough and Softouch, Video, Published Sep. 30, 2015, https://www.youtube.com/watch?v=C9ngfY97Bkg.

\* cited by examiner

2300

2302
Calculating, by at least one computing unit, a pose of a target in upto 6DOF using optical measurements generated by a sensor, the sensor comprising an optical sensor in communication with computing unit

2304
Determinig an expected location of the effector of a tool based on pre-loaded information of the tool, the sensor configured to attach to the tool at a known positional relationship

2306
Determining a location of the effector of the tool based on features detected from an optical sensor image generated by the optical sensor

2308
Calculating a difference between the location and the expected location of the effector of the tool

2310
Generating a confidence metric using the difference

Figure 23

DEVICES, SYSTEMS AND METHODS FOR NATURAL FEATURE TRACKING OF SURGICAL TOOLS AND OTHER OBJECTS

CROSS-REFERENCE TO RELATED APPLICATIONS

This application is a continuation of U.S. application Ser. No. 15/522,559, (the '559 application) filed under § 371(c)(1) on Apr. 27, 2017 from PCT No. PCT/CA2015/000560 filed Oct. 29, 2015. The entire contents of the '559 application are incorporated herein by reference. The '559 application claimed priority to U.S. provisional application No. 62/072,041 titled "Systems, methods and devices for anatomical registration and surgical localization" and filed on Oct. 29, 2014, the entire contents of which are incorporated herein by reference.

The '559 application claimed priority to U.S. provisional application No. 62/072,030 titled "Devices including a surgical navigation camera and systems and methods for surgical navigation" and filed on Oct. 29, 2014, the entire contents of which are incorporated herein by reference.

The '559 application claimed priority to U.S. provisional application No. 62/084,891 titled "Devices, systems and methods for natural feature tracking of surgical tools and other objects" and filed on Nov. 26, 2014, the entire contents of which are incorporated herein by reference.

The '559 application claimed priority to U.S. provisional application No. 62/072,032 titled "Devices, systems and methods for reamer guidance and cup seating" and filed on Oct. 29, 2014, the entire contents of which are incorporated herein by reference.

FIELD

The present disclosure relates to systems, methods, and devices for tracking of features of tools by an optical tracking system for the purpose of calibration of tools, verification of the calibration and registration of an anatomy.

BACKGROUND

In many types of surgery, systems and devices are used to provide a surgeon with real-time positional guidance to guide therapy. For example, in THA, there exist systems that provide a surgeon with positional guidance of an acetabular implant with respect to a pelvis of a patient. Positional measurements are measured using tracking systems, typically utilizing optical, electro-magnetic, inertial, ultrasonic or RF measurement modalities.

Optical tracking systems, such as the Polaris™ system, manufactured by Northern Digital Inc. (Waterloo, ON), utilize fixed multi-camera arrays located in an operating room to detect targets within a working volume of the cameras. The targets normally have optically identifiable markers that are easily identifiable in a video feed of the cameras. Examples of markers include active or reflective markers in the infra-red frequency spectrum, markers of a distinct colour, markers with distinct shapes or patterns, which are easily positively identifiable in an image (e.g. checker pattern) etc. Commonly, reflective spheres are used as markers, since their centroids are well-defined and accurate; furthermore, spheres can be viewed from multiple angles. The markers and the cameras may have matched frequencies to filter unwanted light, either in hardware or in software.

Targets are normally comprised of a plurality of markers. A single marker provides an identifiable feature to the optical tracking system in the form of positional information. A plurality of markers associated with a single target would allow the pose (position and orientation) in up to 6 degrees of freedom (DOF) to be calculated by a computing or processing unit embedded within, or in communication with the optical tracking system. Each marker provides a well-defined and accurate feature. For medical and/or surgical applications, optical tracking systems are generally used to determine the pose of targets and the objects to which targets are attached (e.g. surgical instruments or tools, a patient's anatomy, etc.). Targets (comprised of a plurality of markers) must be registered (also referred to as calibrated) to the instrument to which they are attached; furthermore, they must maintain the registration throughout use.

BRIEF SUMMARY

There is disclosed a system comprising: a sensor comprising an optical sensor configured for attachment to a tool at a known positional relationship, the tool having an effector with the tool lying within a field of view of the optical sensor, the sensor configured to generate an optical sensor image of the tool and to generate optical measurements of a target, the target lying in the field of view of the optical sensor; and a computing unit in communication with the sensor. The computing unit is configured to: calculate a pose of the target in up to six degrees of freedom using the optical measurements; determine an expected location of the effector of the tool based on pre-loaded information of the tool; determine a location of the effector of the tool based on features of the tool detected from the optical sensor image of the tool; calculate a difference between the location and expected location of the effector of the tool; generate a confidence metric using the difference; and provide positional measurements of the effector of the tool with respect to the target, the positional measurements being provided with the confidence metric. The computing unit is further configured to: provide the confidence metric to a display unit to display in one of a numerical or graphical format; and prevent surgical navigation using the positional measurements when the confidence metric is outside of a tolerance range. The computing unit determines the location of the effector of the tool by: calculating a pose of the effector of the tool and further determining the expected location of the effector of the tool by calculating an expected pose of the effector of the tool; and by calculating a position of the effector of the tool within a coordinate frame of the two-dimensional optical sensor image and further determining the expected location of the effector of the tool by calculating an expected position of the effector of the tool within the coordinate frame of the two-dimensional optical sensor image. The target is configured to: attach to an object; attach to an anatomy of a patient; and provide positional information to the optical sensor. The tool contains features that comprise optically detectable markers. The sensor further comprises a kinematic mount to kinematically couple to a cooperating kinematic mount on the tool, and the pre-loaded information comprises a first positional relationship between the optical sensor and the kinematic mount of the sensor, and a second positional relationship between the cooperating kinematic mount and the tool.

There is disclosed a system to provide surgical navigation of an effector tool with respect to the pose of a target. The system comprises: a sensor comprising an optical sensor configured for attachment to the tool at a known positional relationship, the tool having an effector with the tool lying within a field of view of the optical sensor, the sensor configured to generate an optical sensor image of the tool and to generate optical measurements of the target, the target lying in the field of view of the optical sensor; and a computing unit in communication with the sensor. The computing unit is configured to: calculate the pose of the target in up to six degrees of freedom using the optical measurements; determine an expected location of the tool based on pre-loaded information of the tool; generate a virtual tool projection based on the expected location of the tool; generate a composite image comprising the optical sensor image, the virtual tool projection and virtual error bounds; and provide the composite image to a display unit. The system further comprises: a display unit to display the composite image; and a target configured to attach to an anatomy of a patient and provide positional information to the optical sensor wherein the computing unit is configured to provide surgical navigation with respect to the target. The sensor further comprises a kinematic mount for attachment to a cooperating kinematic mount on the tool, and the pre-loaded information comprises a first positional relationship between the optical sensor and the kinematic mount of the sensor, and a second positional relationship between the cooperating kinematic mount and the tool. There is an optically detectable marker attached to the tool, and the computing unit is further configured to determine the expected location of the tool based on the pre-loaded information of the tool, the pre-loaded information comprising a spatial relationship between the sensor and the optically detectable marker, and the virtual tool projection comprising a virtual projection of the optically detectable marker.

There is disclosed a computer-implemented method capable of: calculating, by at least one computing unit, a pose of a target in up to six degrees of freedom using optical measurements, generated by a sensor comprising an optical sensor, the sensor in communication with the computing unit, the target lying in a field of view of the sensor; determining, by the at least one computing unit, an expected location of an effector of a tool, with the tool lying within the field of view of the sensor, based on pre-loaded information of the tool, the sensor configured to attach to the tool at a known positional relationship; determining, by the at least one computing unit, a location of the effector of the tool based on features detected from an optical sensor image of the tool generated by the optical sensor; calculating, by the at least one computing unit, a difference between the location and the expected location of the effector of the tool; generating, by the at least one computing unit, a confidence metric using the difference; and providing positional measurements of the effector of the tool with respect to the target, the positional measurements being provided with the confidence metric.

There is disclosed a computer-implemented method to provide surgical navigation of an effector of a tool with respect to a pose of a target by: calculating, by at least one computing unit, the pose of the target in up to six degrees of freedom using optical measurements generated by a sensor comprising an optical sensor, the sensor in communication with the computing unit, and the target lying in a field of view of the sensor; determining, by the at least one computing unit, an expected location of the effector of the tool, with the tool lying within the field of view of the sensor, based on pre-loaded information of the tool, the sensor configured to attach to the tool at a known positional relationship; generating, by the at least one computing unit, a virtual tool projection based on the expected location of the effector of the tool; generating, by the at least one computing unit, a composite image comprising an optical sensor image generated by the optical sensor and the virtual tool projection; and providing the composite image to a display unit.

There is disclosed a system comprising: a sensor comprising an optical sensor configured to generate optical measurements of a target and simultaneously generate an optical sensor image of an anatomy of a patient; a target configured to be attached to the anatomy; and a computing unit in communication with the sensor. The computing unit configured to: calculate a pose of the target attached to the anatomy using the optical measurements; measure spatial attributes of the anatomy using the optical sensor image; and determine a registration for the anatomy based on the pose of the target and the spatial attributes of the anatomy. The sensor is further comprised of a depth sensor to generate a depth image, wherein the depth sensor is: one of a time of flight camera, a laser scanner, and a camera with illuminating components; and in a known and fixed relationship with respect to the optical sensor. The computing unit is further configured to: measure the spatial attributes of the anatomy additionally using the depth image; determine a 3D surface profile of the anatomy based on the spatial attributes; determine the registration of the anatomy using a plurality of poses of the target and optical sensor images from a plurality of vantage points; determine the 3D surface profile of the anatomy using a plurality of poses of the target and depth images from a plurality of vantage points; and use a digital 3D scan of the anatomy and a correspondence between the optical sensor image and the digital 3D scan to determine the registration for the anatomy.

There is disclosed a sensor, in communication with a computing unit, to provide surgical navigation. The sensor comprises: a first optical sensor configured to generate optical measurements of a target and with a first field of view; and a second optical sensor located at a known and fixed positional relationship from the first optical sensor, and further configured to generate optical measurements of features of an object and with a second field of view, the second field of view overlapping with the first field of view. The first optical sensor and the second optical sensor share at least one optical component, the optical component being one of an imager and a lens. The first optical sensor and the second optical sensor are a single optical sensor. The sensor further comprises a depth sensor, the depth sensor configured to: be positioned in a known and fixed relationship with respect to the first optical sensor and the second optical sensor; and have an overlapping field of view with the first field of view and the second field of view. The sensor is configured for attachment to an anatomy of a patient and further comprises a kinematic mount for mounting to a cooperating kinematic mount.

BRIEF DESCRIPTION OF DRAWINGS

Embodiments disclosed herein will be more fully understood from the detailed description and the corresponding drawings, which form a part of this application, and in which:

FIGS. 23 and 24 show flowcharts of respective methods, in accordance with embodiments.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

Optical Tracking Systems—Introduction

Several systems, methods and devices will be described below as embodiments. The scope of the claims should not be limited by the embodiments set forth in the examples, but should be given the broadest interpretation consistent with the description as a whole.

Reference in the specification to "one embodiment," "preferred embodiment," "an embodiment," or "embodiments" means that a particular feature, structure, characteristic, or function described in connection with the embodiment is included in at least one embodiment, and may be in more than one embodiment. Also, such phrases in various places in the specification are not necessarily all referring to the same embodiment or embodiments.

Figure 1:
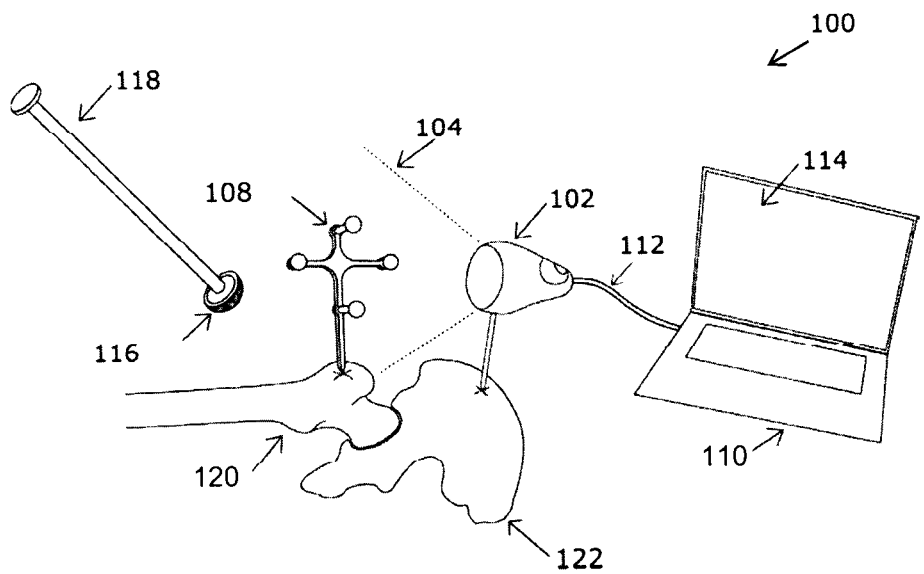
FIG. 1 depicts a surgical tracking system with a sensor for use in a sterile field, with a target in a field of view of the sensor.

An optical surgical tracking system has been described in previously filed patent documents (for example, see applications U.S. 20120157887 titled "Method and system for aligning a prosthesis during surgery using active sensors", the entire contents of which are incorporated herein and U.S. 20140275940 titled "System and method for intra-operative leg position measurement", the entire contents of which are incorporated herein). An exemplary system applied to Total Hip Arthroplasty (THA) may be seen in FIG. 1. This optical tracking system 100 comprises a sensor 102, further comprising an optical sensor (such as, a camera) with a field of view (FOV) 104. The sensor 102 may be attached to objects 106 such as, a patient's bone and surgical tools and instruments. The system also comprises one or more targets 108. The targets 108 can be tracked by the optical sensor when the target 108 lies in the FOV 104 of the optical sensor to calculate pose (position and orientation), and can also be attached to various objects, including patient anatomy, tools and instruments. The sensor 102 is in communication with a computing or processing unit 110 via a cable 112. The system may include a display unit 114 to display measurements obtained from the pose of the targets 108 to a surgeon. In this example, an acetabular implant 116 is shown attached to its insertion tool 118, referred to as an acetabular impactor. The target 108 is attached to a femur bone 120, and the sensor 102 is attached to a pelvis 122.

This present disclosure uses THA as an illustrative example; however, it must be appreciated that the present disclosure extends to all medical interventions where real-time positional measurements of objects are valuable. Objects 106 are intended to be surgical tools or instruments, or parts of the anatomy of a patient. Furthermore, in some of the present examples, the sensor 102 will be shown as attached to a patient's pelvis 122 located in a surgical sterile field. It must be appreciated that this disclosure is not limited to attaching the sensor 102 to the bone of a patient; however, there may be advantages in doing so, such as, the inherent close proximity between the optical sensor and the objects being tracked.

In this specification, the sensor 102 is used for measurement of poses of targets 108 attached to objects 106 that are within its field of view 104. It is not a medical imaging or visualization device, such as an ultrasound probe or an endoscope. The optical sensor requires an optical calibration, as well as a rigid construction to maintain the calibration, to enable precise pose measurements of a target.

Optical Tracking Based on Natural Features of an Object

Figure 2:
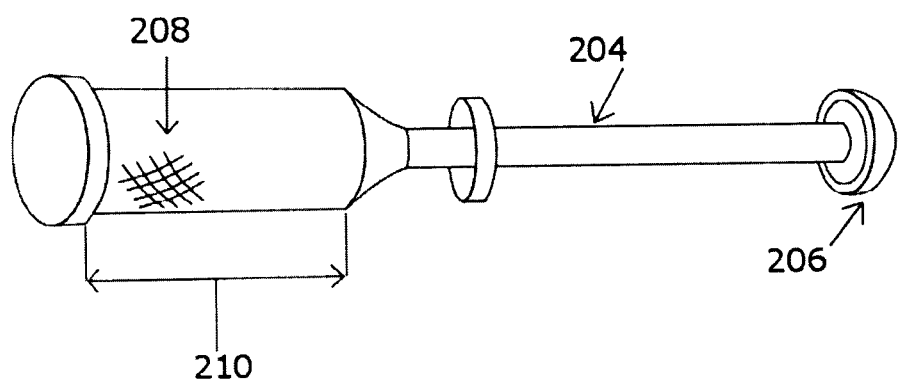
FIG. 2 illustrates an impactor tool highlighting its geometrical features as an example for clarity.

Prior art discloses targets, comprising a plurality of optically detectable markers, that are attached to objects, including tools, instruments and anatomy in navigated surgical procedures. As illustrated in FIG. 2, the object 106 may be an acetabular impactor 202. Instead of using a target 108 to track the impactor 202, the natural features of the impactor may be used to track it. Natural feature tracking (NFT) aims at determining the pose of an object using an optical sensor to identify natural features associated with the object (natural features being inherent spatial features of the object itself, as opposed to a target, whose fundamental purpose is to provide positional signals for calculation of positional measurements). The natural features are processed by a computing unit 110, and pose measurements are computed. For example, an impactor 202 may have known features, which could be identified in a two-dimensional optical sensor image, and used to determine the pose of the impactor in up to 6 DOF using the natural features. Impactors often have a straight cylindrical shaft 204 along the same axis as the acetabular implant; the acetabular implant 206 itself is hemispherical, such that it has an opening plane as well as a centroid; impactors may have other features, such as changes in shape or diameter; sections of an impactor may be textured or coloured 208; sections of an impactor may be of known dimensions 210 (e.g. length). All of these exemplary natural features have a particular spatial relationship to the overall pose of the impactor.

In many applications, a 6 DOF pose of an object is not required to provide clinically useful measurements. For example, since the acetabular implant 206 is hemispherical, its orientation about the axis of its opening plane is not important. Therefore, when aligning the acetabular cup 206, only 2 DOF in orientation are useful. Since in THA, the angle of the cup 206 as it is placed inside the pelvis 122 is important (and not necessarily the translational position), a relevant pose measurement would include only 2 DOF. In the context of this specification, tracking the natural features of the object 106 may include the determination of a pose of an object 106 in up to six degrees of freedom.

Figure 3A:
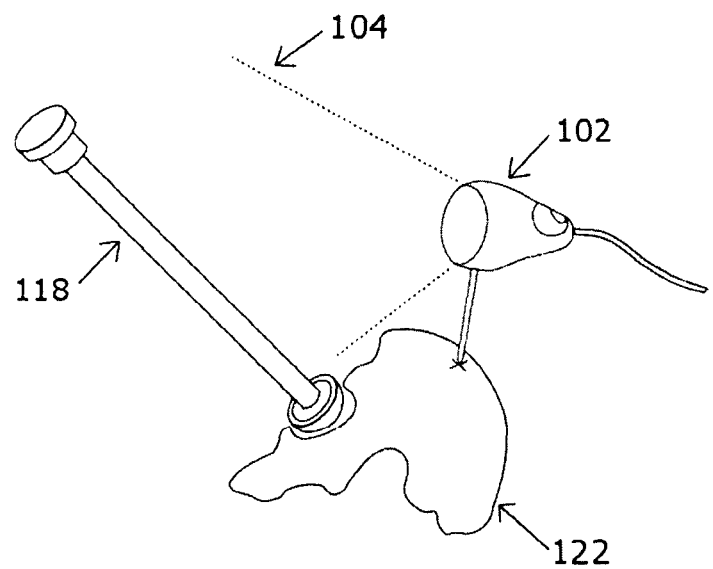
FIG. 3a depicts a surgical tracking system with a sensor to track a tool without a target, and using only features of the tool, in accordance with an embodiment.
Figure 3B:
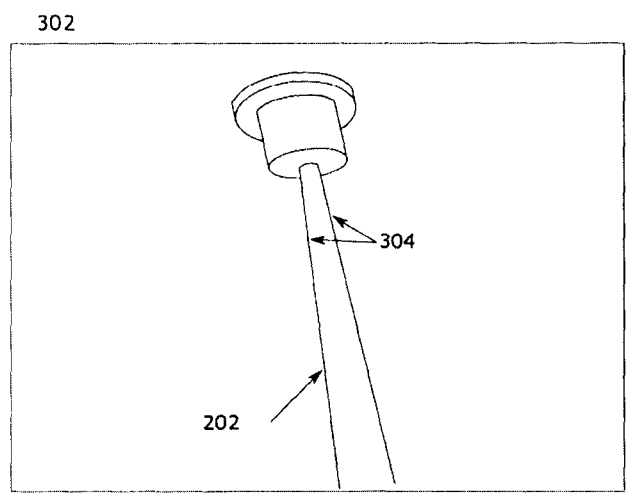
FIG. 3b depicts an image of a field of view of the optical sensor, when the sensor is pointed at the tool (as shown in FIG. 3a)

FIG. 3a and FIG. 3b illustrate an example of THA during which NFT is applied to the step of guiding the insertion of an acetabular cup 206 using an impactor tool 202. An impactor 202 is within a FOV 104 of an optical sensor attached to a pelvis 122 as the surgeon is positioning the impactor 202. The two-dimensional optical sensor image 302 as seen by the optical sensor is shown in FIG. 3b. In this figure, the optical sensor image 302 of the impactor is depicted. The image 302 contains many features that may be extracted using image processing operations. For example, the straight edges 304 of the cylindrical shaft 204 may be detected using edge detection operations. Due to the perspective effect, the edge lines of the shaft 204 will not be parallel, but rather angled towards a vanishing point; the two lines as projected onto the image, as well as the angle between them, can be used to calculate the 2 DOF orientation of the impactor (in real time). These measurements can be displayed to a surgeon who is using the system 100 to accurately place the implant 206 within a patient's pelvis 122 at a particular desired angle. The edges of the straight cylinder are exemplary features; any other identifiable feature may be used.

Due to the close proximity of the sensor to the surgical objects being tracked, NFT may be used favourably in the optical tracking system described herein. In a traditional optical tracking system disclosed by prior art, where the cameras are located outside a sterile field of a surgery, the working volume of the cameras is quite large, and being able to accurately and positively track a surgical object using NFT is not feasible. Conversely, when the camera is in close proximity to the tracked objects, the tracked objects provide more information within the camera image, which can be used for accurate and repeatable localization. To aid in the identification of objects within the image, the sensor may comprise illuminating components, such as, infra-red LEDs to illuminate a scene containing the object of interest, thus enhancing the information content within the image by which the optical sensor is able to accurately track the object via its natural features. Furthermore, where the optical sensor is in close proximity to the target (e.g. when it is attached to the patient's anatomy), further benefits arise, such as, a more pronounced visual perspective effect, which may aid in the pose calculation using NFT.

NFT Based on a Priori Feature Information

Figure 4:
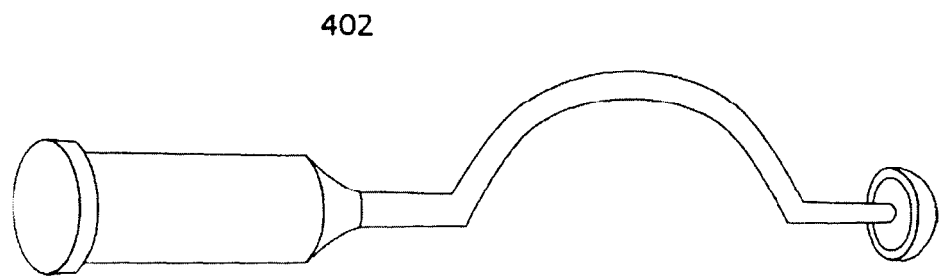
FIG. 4 illustrates a curved impactor tool highlighting its geometrical features as an example for clarity.

To calculate the pose of an object based on NFT, information about the features of the object may be known a priori. For simple objects, such as a straight impactor (or for example, a biopsy needle), the a priori information may be that the tool is a straight shaft. This information can be used by the image processing and pose solving operations (executing on a computing unit) to calculate pose of the object. In some cases, objects may have complex feature definitions. For example, as illustrated in FIG. 4, in THA, a curved impactor 402 may be used. Complex shapes of the object may require more complex a priori feature information to be available to the image processing and pose solving operations. To address this issue, pre-loaded feature information may be accessed by the computer operations, such information being specific to the object or class of objects being tracked. The pre-loaded feature information may be in the form of electronic Computer-Aided Design (CAD) files, stored in memory on the computer. A database of CAD files for various tools or objects may be stored in memory (or accessed via a network) to provide the image processing and pose solving operations with this information. The pre-loaded information may include the geometry or shape of the object. Where the object is a tool, and the tool has an effector, pre-loaded information may include the positional relationship of the effector of the tool with respect to other parts of the tool. An effector of a tool is a part of the tool that has the greatest effect in achieving its purpose, e.g.: blade of a scalpel, tip of a probe, etc.

The operations use the pre-loaded information to assist in determining the pose of the object. For example, the operations, executing on a computing unit, may receive a raw image from the optical sensor (optical sensor image), process the optical sensor image to identify features to be used as an input, load a priori feature information of the object, perform optimization operations to match identified input features with a priori feature information and if a suitable match exists, calculate the pose accordingly.

In some instances, the a priori feature information may not be available. In such a case, the feature information may be generated in advance of the real-time pose measurements, by "teaching" the system the features of the object. For example, multiple views of an object (e.g. impactor tool) may be captured through the optical sensor from different vantage points. Key features (e.g. shaft axis) may be identified automatically (i.e. by the computing unit), semi-automatically (i.e. by the computing unit with limited user intervention) or manually (i.e. by the user, for example, identifying specific features by clicking on them on a computer screen) and saved in software (e.g. in computer memory). These features may now be accessed for use in pose solving operations as described above.

Natural Feature and Target Tracking (Serial)

In some instances, it may be appropriate for the system 100 to track both natural features of an object and targets attached to the same or different objects at different steps during navigated surgery. For example, in THA, NFT may be useful for angular measurements used in placing an acetabular cup 206 in a pelvis 122, but not for measuring changes in leg position. This is because a femur 120 may not possess clearly defined features that can be detected by the optical sensor and/or processed by operations for pose calculation. Whereas an impactor shaft 204 is a well-defined and unambiguous shape, a femur 120 is irregularly shaped, covered in soft tissues and blood, and varies from patient to patient. Therefore, it is appropriate to track a patient's leg position in THA using a target 108, while it remains advantageous to track an impactor 202 without a target, for simplicity, ease of use and accuracy. In reference to FIG. 1, a femur 120 is tracked with a target 108, whereas an impactor 202 is depicted without a target. There are many examples outside of THA in which it is appropriate to track certain objects with a target, and others via NFT, during the same procedure, using the same system.

In order to track both targets and natural features using the same system, the system is capable of detecting a target and the natural features of an object. Either both can be detected within the same optical spectrum (e.g. visible, infra-red, etc.) or the optical sensor can detect the target and the natural features separately (e.g. in different spectra—infra-red spectrum for markers on a target, visible spectrum for natural features), but relative to the same coordinate baseline reference of the optical sensor. Further detail on this point is included below.

NFT of an Object Using its Natural Features and a Target

Figure 5:
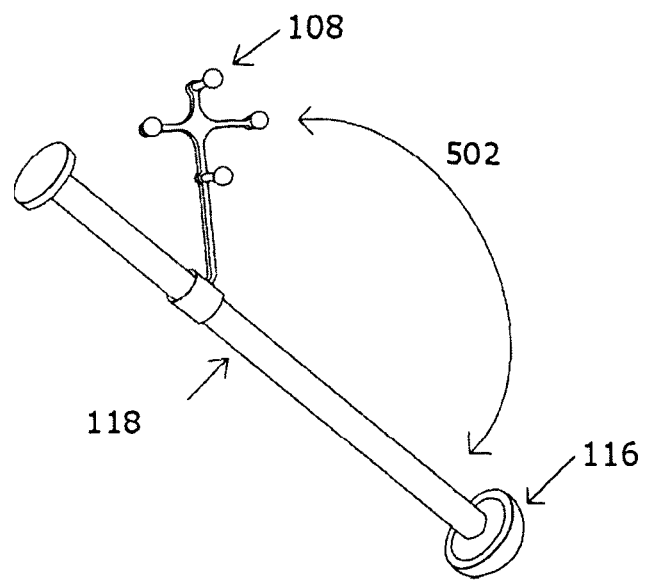
FIG. 5 illustrates a registration between a target attached to a tool, and a feature of the tool, as an example for clarity.

In one embodiment, the system 100 tracks natural features and targets simultaneously. The natural features may be of an object to which the target 108 is coupled. For example, the system may provide functionality to calibrate an impactor tool, in which a positional relationship 502 between an implant (e.g. acetabular cup) and a target is to be determined. FIG. 5 illustrates an impactor tool 202 with an attached acetabular implant 206 and a target 108 attached thereto. This tool 202 is used when inserting the acetabular implant 206 during THA. In order to calibrate the tool 202, the sensor 102 may track the target 108, and simultaneously track natural features of the acetabular implant 206.

Figure 6:
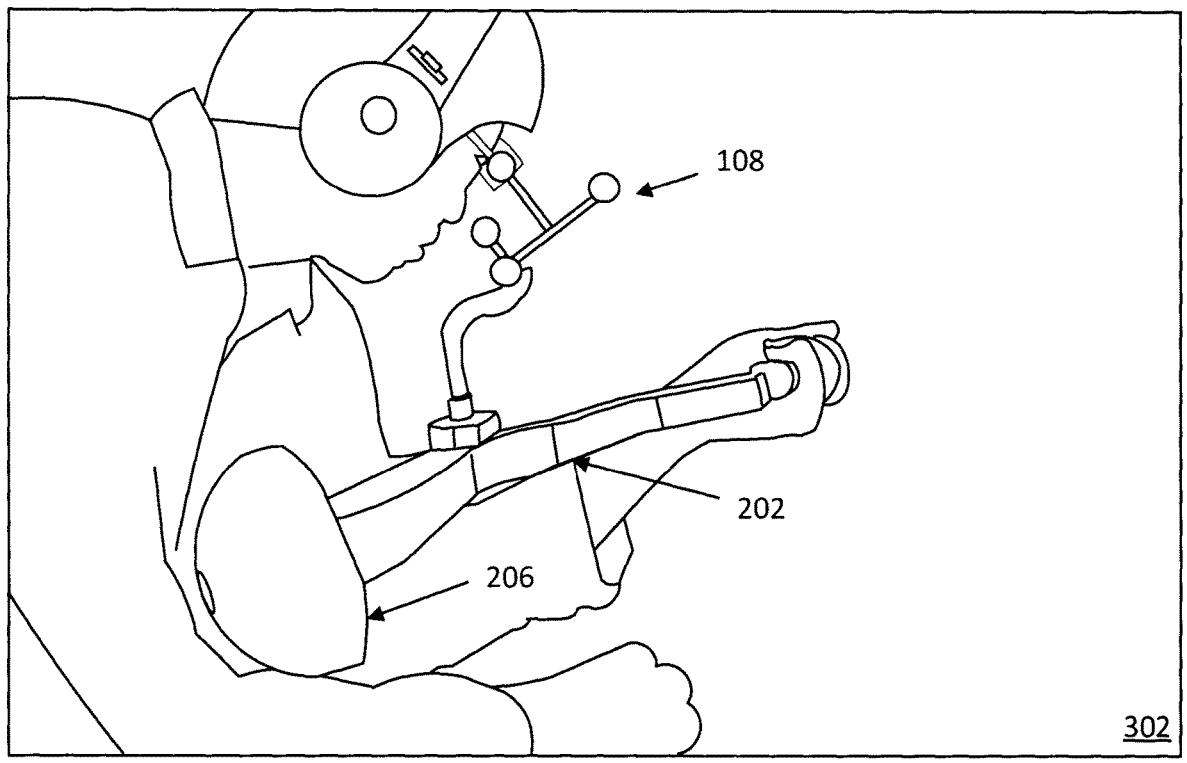
FIG. 6 depicts a photograph of an actual optical sensor image when viewing an impactor tool with a target and an implant attached to it.

FIG. 6 shows an image 302 from a video feed of the sensor 102 in which a target 108 and an implant 206 are both attached to an impactor 202 and are visible to the sensor. A step of calibration to determine the positional relationship 502 between the target 108 and the implant 206 may be performed by tracking the target 108, as well as tracking features on the implant 206 such as, its centroid, diameter, opening plane, etc. In this example, the implant 206 is the effector of the impactor 202. Calibrating this object involves determining the relative pose of the implant and the target, which may be computed by simultaneously calculating the pose of the target and implant individually, and then determining a spatial transformation to relate their respective coordinate systems. In one embodiment, multiple views of the target and implant from different vantage points may reduce the computational complexity of the pose solving operations that are executed to determine the positional relationship 502 between the implant 206 and the target 108.

This scenario may arise for several reasons, for example: it may be difficult to determine the pose of the object depending on the angle from which the natural features are being viewed; it may be difficult to determine the pose of the object based on its geometry (e.g. determining the orientation of a substantially spherical object); there may be sparse a priori information available about the natural feature geometry. In such cases, multiple views from multiple vantage points of the sensor may help provide more information content about the natural features of the effector itself, as well as the spatial relationship between the effector and the target. It will be appreciated by those skilled in the art that this increased information content is helpful in accurately measuring the pose of the effector, as well as the relative pose of the effector and target.

Target on Object: Verification of Calibrated Positional Relationship

Figure 7A:
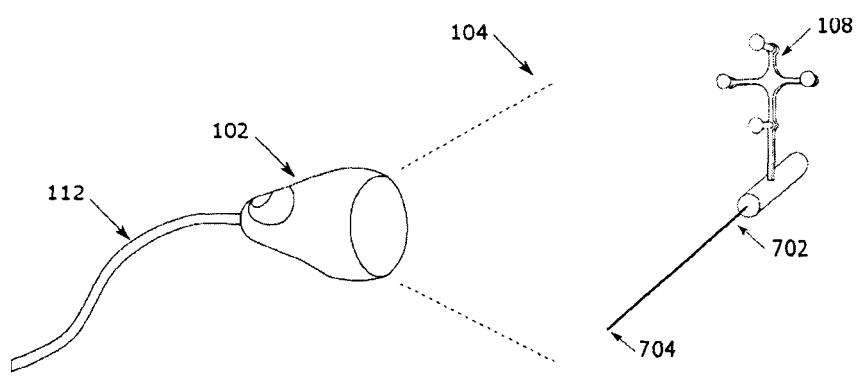
FIG. 7a illustrates a sensor pointing at a tool with a tip, and a target.
Figure 7B:
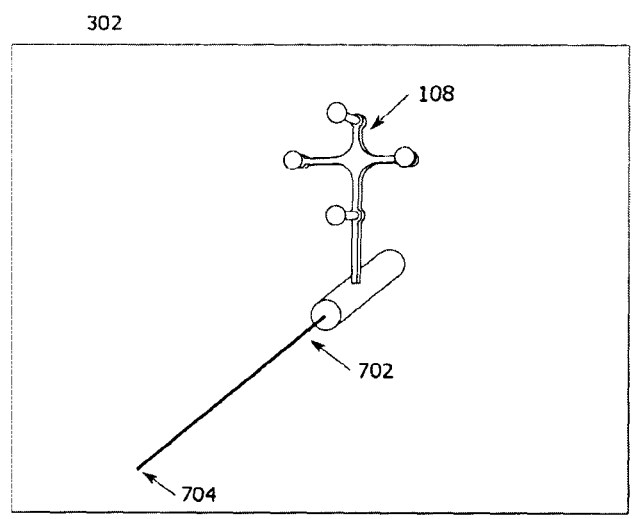
FIG. 7b is a line drawing showing a representative optical sensor image of the sensor pointing at the tool with a tip, and a target.

In addition to calibrating objects prior to use, simultaneous tracking of the object and the target can provide a run-time accuracy check to ensure that the object is still calibrated, based on pre-loaded information representing the expected spatial relationship between the target and the object (e.g. tool). Pre-loaded information may be made available to a computing unit any time prior to verification of the calibration. The pre-loaded information may be based on a previously performed calibration, manufacturing tolerances and geometry, generated feature information through the previously-described learning process, etc. For example, the target may be used for pose calculation of the object (in this case, an instrument), and the natural features may be tracked redundantly to provide a confidence metric that the instrument remains calibrated. Using a navigated biopsy as an exemplary surgical procedure, FIG. 7a illustrates a sensor 102 with a field of view 104 within which there is a biopsy needle 702 and its tip 704. There is a target 108 attached to a handle 706 of the needle 702. The tip 704 of the needle 702 itself may be tracked to ensure that it remains correctly positioned with respect to the target 108. FIG. 7b shows a two-dimensional image 302 as seen by the optical sensor with the tip 704 in a calibrated position with respect to the target 108. The sensor 102 is able to detect the target 108 in the scene, as well as detect a location of the effector 704 of the needle 702 based on its natural features (e.g. in this case, the effector being the tip 704—the end point of a long straight shaft). The natural feature information may be available a priori or be taught to the system 100, as described in previous embodiments. The detected tip position is the location of the effector. A computing unit in communication with the sensor computes a pose of the target 108, and determines a calculated tip position (i.e. expected position where the tip is expected to be). The calculated tip position relies on a priori knowledge of where the tip is expected to be spatially with respect to the target (in general, the tool may attach to the target according to a known positional relationship). This a priori knowledge may be from a previously-performed calibration, or based on expected spatial relationships from manufacturing tolerances of the target and/or tool. The a priori knowledge is preferably accessible to the computing unit as pre-loaded information. The calculated tip position may be compared with the detected tip position to calculate a difference, if there is one. This difference is used to generate a confidence metric. The comparison may be performed by the computing unit. After comparison, if the confidence metric is within a tolerance range defined for a particular application of the system, the system 100 may display results of the verification of calibration or display measurements accordingly in a numerical or graphical format, as described below. Furthermore, the computing unit 110 may alert the user that the needle 702 is out of calibration such that the user can take appropriate steps (e.g. discard needle, recalibrate needle, etc.), also described below.

The computing unit may provide a confidence metric based on the calibration verification results. The confidence metric may represent a confidence of the accuracy of the positional localization of the effector of the tool. The confidence metric may be provided to a display unit for display to a user based on which the user may adjust their usage of the system. For example, the user may choose to perform a re-calibration or discontinue use of the system if the localization confidence is low). The confidence metric may be displayed graphically, numerically, or in any other suitable fashion.

Furthermore, calibration verification results and/or a confidence metric may be provided for further processing such that the surgical navigation (e.g. navigation and/or robotic surgery) system takes appropriate action. For example, in the event of compromised calibration (e.g. low confidence metric), the computing unit may discontinue providing positional measurements to a display unit (in this way, the user would be prevented from seeing potentially inaccurate positional measurements related to the effector). In another example, in a robotic surgery application, a compromised calibration may cause the processing unit to send instructions to prevent the robot from proceeding with its planned trajectory (which would potentially cause harm to a patient, as the robot would be relying on inaccurate positional measurements related to the effector).

Figure 8A:
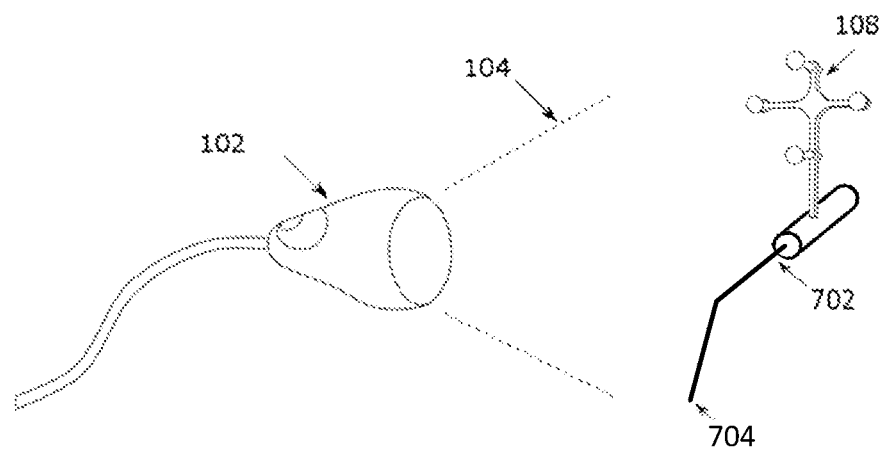
FIG. 8a illustrates a sensor pointing at a tool with a bent tip, and a target.
Figure 8B:
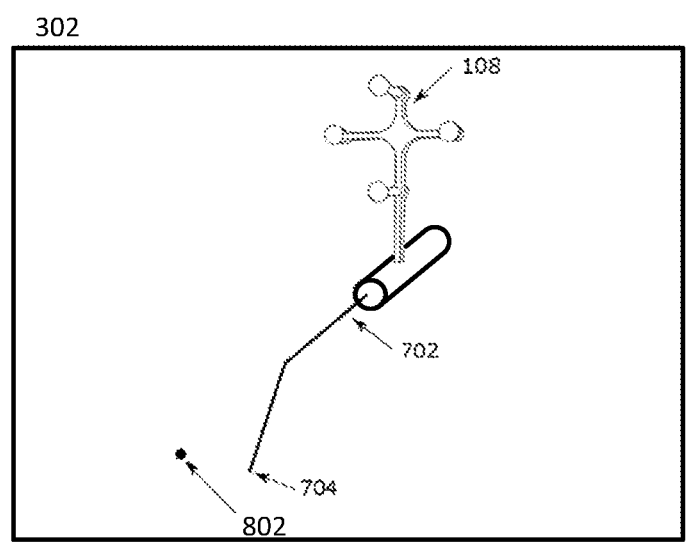
FIG. 8b is a line drawing showing a representative optical sensor image of the sensor pointing at the tool with a bent tip, and a target.

For further clarity, FIG. 8*a* illustrates a sensor 102 with a field of view 104 within which there is a biopsy needle 702 that is bent with its tip 704 in a location that is different from its expected location. In addition, there is a target 108 attached to a handle. FIG. 8*b* depicts a two-dimensional image 302 as seen by the optical sensor. As depicted, the actual tip 704 of the needle 702 is not where it is expected to be, with respect to the target 108. The sensor 102 is able to detect the pose of the target 108, as well as detect the tip 704 of the needle 702 based on its natural features. The sensor 102 is able to determine a calculated tip position 802 and the expected calibration between the target and the tip. The computing unit may perform operations to verify the calibration of the tool, which would determine whether the tool (i.e. the needle) is out of calibration.

According to this embodiment, the natural features need not be tracked in 6 DOF. The number of DOF that are tracked by a sensor may depend on the requirements of the application. For example, where the orientation of the shaft of the needle does not matter for the application, only the 3 DOF related to a position of the tip of the needle tip may be desirable. Conversely, where the orientation of the shaft is required for the application, then 5 DOF needle tracking may be desirable: 3 DOF for position, and 2 DOF for orientation (the $3^{rd}$ orientation degree of freedom being rotation about the axis of the shaft, which do not need to be measured since the shaft is symmetrical about this axis).

Furthermore, rather than measure the pose of the object based on its natural features in up to 6 DOF in a world coordinate reference frame (WCRF) (i.e. physical space), it may be desirable to measure the position of the object (e.g. needle) in a coordinate frame of the two-dimensional image as seen by the optical sensor in the optical sensor image frame (OSIF). Note: the WCRF and OSIF are related: objects in the WCRF are projected as a 2-dimensional optical sensor image, depending on the specifications of the optical sensor, e.g.: type of lens, optical length, etc. The advantage of measuring the object's position in the OSIF rather than WCRF, is that it may be simpler to measure the object's positional features in the OSIF as fewer calculations are required to be executed (e.g. pose calculation may not be required).

For example, a method to verify calibration of a tool and its effector may be implemented by the computing unit and applied to the example of the biopsy needle is provided below. The computing unit receives a sensor image that includes target and the natural features of the needle (including needle tip), detects the target (attached to the needle), calculate pose of the target in WCRF, based on a priori feature information of the needle itself, as well as the pose of the target in WCRF, determine expected pose of the tip of the needle, project the expected pose of the calculated needle tip into the OSIF, detect the actual position of the tip of the needle in OSIF, and compare calculated and detected needle tip positions in OSIF and provide the difference. The difference may be displayed on a display unit. The difference may be displayed graphically or numerically.

Target on Object: Verification of Calibration by User

In another embodiment for verification of the calibration of a tool, a system displays to a user (via a display unit) an image as seen by the optical sensor. This may be done in the form of a video feed of images as seen by the optical sensor. With pre-loaded information about the spatial features of a tool and its effector, the system can display to the user an expected image of the tool in the format of a two-dimensional image in OSIF, based on the pose of the target attached thereto. A user is then able to compare the location of the tool with the expected location of the tool, as depicted in the image of the optical sensor. In this embodiment, the computing unit does not need to execute operations to identify natural features in the optical sensors image; instead, a user is able to visually identify the object's natural features. This method may provide a sense of confidence to a user, as they are able to verify the accuracy of the calibration of a tool themselves, by visually comparing the actual and expected locations of the tool's effector. This embodiment may further involve displaying a virtual tool projection (i.e. a computer generated representation of the tool's features of interest). The virtual tool projection is based on the pose of the target, and graphically represents where the computing unit expects the tool to be within the image. The virtual tool projection may be overlaid or superimposed on the images from the optical sensor and displayed to the user as a composite image, which also display the natural features of the tool itself. The user may then visually compare the natural features of the tool with the virtual tool projection, and verify whether they are sufficiently aligned.

Figure 9:
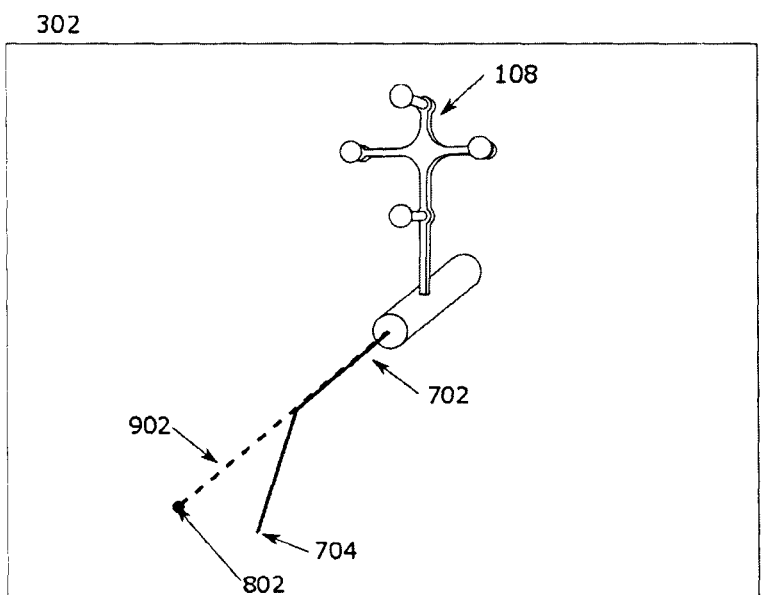
FIG. 9 is a line drawing showing a representative optical sensor image of the sensor pointing at the tool with a bent tip, a virtual projection of where the tip should be, and a target attached to the tool.

For example, with respect to needle navigation, FIG. 9 shows an image 302 as seen by the optical sensor including a target 108 attached to the needle 702. The needle has a tip 704 and an axis. The tip 704 of the needle 702 is bent. The figure also shows a virtual tool projection 902, based on the pose of the target 108. Because the needle 702 is bent, the virtual tool projection 902 is not aligned with the actual needle 702. A user may visually detect that the virtual needle and the actual needle are not in alignment, and proceed accordingly.

A computing unit method associated with this embodiment comprises receiving an optical sensor image comprising a target and natural features of interest of an object, detecting the pose of the target, calculating pose of the target in WCRF, determining pose of object based on target pose in WCRF, generating a graphical representation (virtual projection) of object based on object pose projected into OSIF and pre-loaded feature information of the object, and providing display information in the form of a composite image comprising the optical sensor image with superimposed virtual projection of the object. The user is then able to compare object natural features of interest with virtual object projection to verify calibration.

Figure 10:
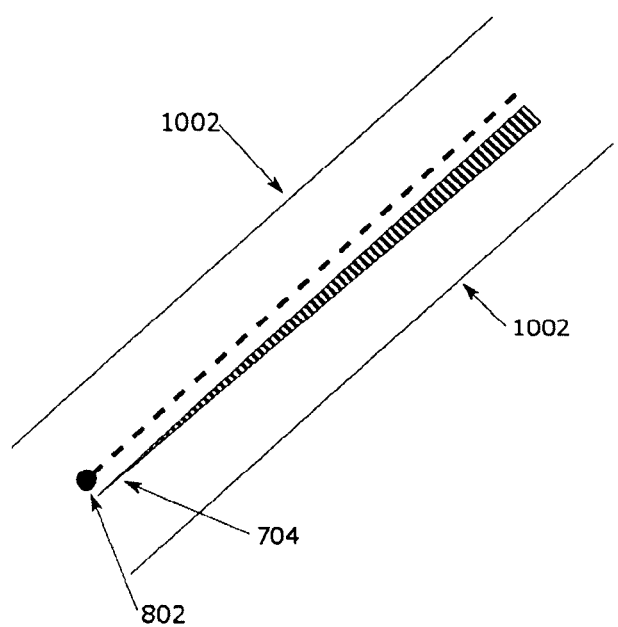
FIG. 10 depicts, as an example for clarity, virtual error bounds projected on a composite image of a tip of a tool.

This embodiment may provide further features to aid a user in assessing the calibration of the object. For example, as illustrated in FIG. 10, the computing unit 110 may further generate virtual error bounds 1002 for display. The virtual error bounds 1002 may be used to assess the degree to which the object (e.g. tool, instrument, etc.) is out of calibration, when the object in the optical sensor image 302 is not in alignment with the virtual projection 902. For example, in FIG. 10, the object is not in perfect alignment with the virtual projection, but the object lies within the virtual error bounds. The virtual error bounds 1002 are depicted as lines in FIG. 10; however, there may be any other appropriate shape (or visual element) to represent an acceptable accuracy of the object. For example, the virtual error bound 1002 may be a bounding volume around an implant; a sphere (projected on the image as a circle) around the tip of an instrument; etc. Also, the virtual error bounds 1002 may be tied to a geometrical tolerance in 3D space (e.g. it may be important that the tip of a probe be within a 2 mm sphere). The virtual error bounds may be applied in 3D space (that is, within the WCRF), but displayed as a 2D projection onto the image (that is, on the OSIF). In this way, the virtual error bounds 1002 are scaled according to their desired accuracy tolerance in 3D space.

NFT of Sensor-Mounted Tool+Simultaneous Target Tracking

Figure 11A:
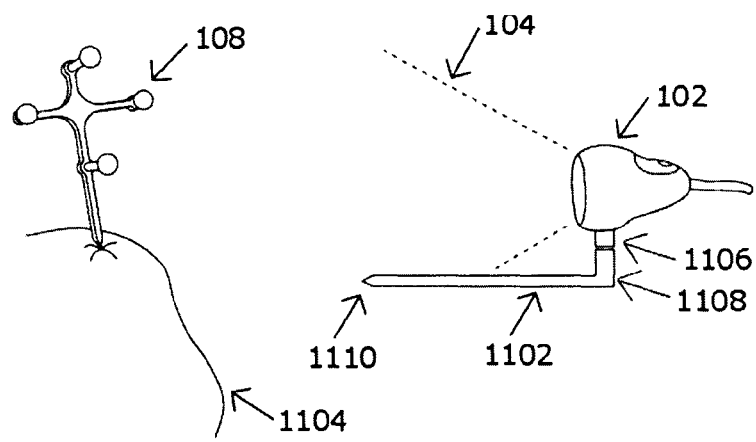
FIG. 11a shows a sensor kinematically coupled to a probe and a target attached to a patient's body at an anatomical feature of interest as an example for clarity.

In one embodiment, natural features of an object coupled to the sensor are detected and used for improved localization with respect to a pose of a target. Reference is now made to FIG. 11a in which the object is a tool. The tool is a probe 1102 that is used to localize an anatomical landmark or feature 1104, e.g. on a bone, within a body cavity, or a lesion within soft tissues in the brain, is attached to the sensor 102. A target 108 is attached to the anatomical feature 1104. The probe 1102 may be kinematically coupled with the sensor 102 through a kinematic mount 1106 on the sensor and a cooperating kinematic mount 1108 on the probe 1102 such that, when in calibration, the sensor 102 and the tip 1110 are in a known positional relationship in up to 6 DOF (comprising a first positional relationship between the sensor 102 and its kinematic mount 1106, and a second positional relationship between the probe 1102 and its kinematic mount 1108) with respect to the sensor 102. More generally, where kinematic mounts are not used, the sensor may attach to the tool according to a known positional relationship (a known positional relationship being any location that may be made known to the computing unit via the pre-loaded information prior to performing a calibration verification). When the probe 1102, with its tip 1110 is in contact with the anatomical feature 1104, the target 108 is within the FOV 104 of the sensor 102, and a relative pose between the sensor 102 and target 108 is captured.

When the sensor is kinematically coupled to the probe and the features of interest of the probe are within the field of view of the sensor, the sensor may track the natural features of the probe to verify the calibration of the positional relationship between the probe and the sensor. All of the previously-described methods for determining the pose of an object with respect to a sensor based on natural feature tracking may apply. In this embodiment, the sensor and the probe have a constant positional relationship. For this reason, it is not necessary to simultaneously track a target and the natural features of the probe.

Where the tool's features of interest are visible to the sensor when the sensor is coupled to the tool, the sensor may track the natural features of the tool to verify the positional relationship between the sensor and the tool. All of the previously-described methods for determining the pose of an object with respect to a sensor based on natural feature tracking apply. For example, the verification may be performed by a processing unit or via user-assessment. The parameters to verify the calibration may be in expressed in the WCRF or in the OSIF. In this embodiment, the sensor and the instrument/tool have a constant positional relationship. One purpose of this embodiment is to measure the pose between a target and the effector of a tool, using the sensor to localize the target. However, while calibrating or verifying the positional relationship between the tool and the sensor, the target need not be trackable, or even within the field of view of the sensor. This is because the tool and the sensor have a constant/fixed positional relationship, and therefore the tool is visible to the sensor (enabling calibration and/or verification) regardless of whether the target is also visible to the sensor.

Figure 11B:
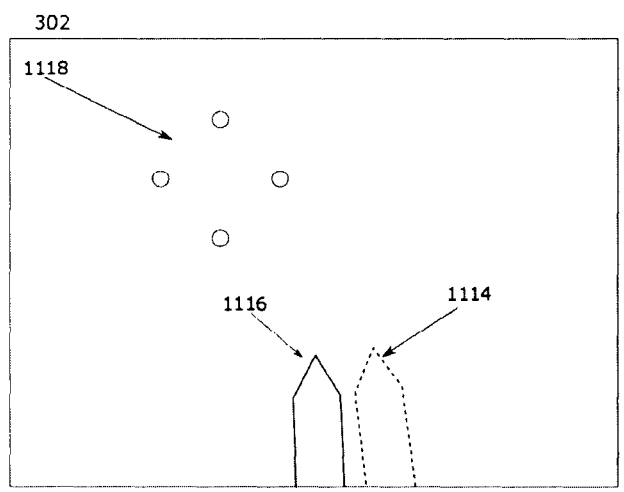
FIG. 11b is a line drawing showing a representative optical sensor image depicting a feature to verify calibration between the optical sensor and the tool.

The verification of the calibration between an effector of a tool, while the tool is attached to a sensor at a known positional relationship in up to 6 DOF, may be used to detect issues with the system's accuracy (e.g. damage to the tool and/or effector, malfunctioning optical system etc.). If the sensor 102 is kinematically coupled to the tool, verification of the calibration may be used to check whether the kinematic coupling is accurate. FIG. 11b illustrates an image 302 as seen by the optical sensor that corresponds to the physical configuration in FIG. 11a. The optical sensor image 302 includes the target 108 within its FOV 104, as well as the tip 1110 of the probe 1102 (via its natural features). A calculated probe tip 1114 is shown in the image 302. The calculated position of the tip of the probe is based on pre-loaded information of the positional relationship between the instrument (e.g. probe) and the sensor. The calculated probe tip 1114 (also called the reference probe tip) represents where the tip is in an accurate calibration. When the location of the probe tip 1116 differs from the expected location of the reference probe tip, the kinematic mount may not being seated properly (if a kinematic coupling exists between the sensor and the probe), there may be a mechanical issue such as, a bent probe tip, or there may be another system inaccuracy. The ability to detect this inaccuracy between the sensor and the tool can prevent incorrect therapy from being delivered to a patient. For example, if the probe is intended for a tumor biopsy, an incorrect kinematic relationship would cause the wrong tissue to be biopsied. The optical sensor image 302 includes a target image 1118. It is noted that the target image 1118 (in FIG. 11b) is not required for calibration and/or verification of the positional relationship between the sensor and the tool (as previously discussed).

A comparison between the actual probe tip 1116 and the calculated probe tip 1114 may be performed by a computing unit, and a difference between the actual pose and expected pose of the tip may be generated. Alternatively, the comparison may be performed by a user, where a virtual tool projection is superimposed on the actual optical sensor image, and displayed to a user as a composite image via a display unit such that the user can visually confirm if the virtual (expected) probe tip is in sufficient alignment with the actual probe tip. As previously described, there are multiple methods to depict the inaccuracy to the user (e.g. virtual error bounds). Furthermore, if the actual tool location (e.g. probe tip) is measured, and the reference tool location (e.g. reference probe tip) is known, the computing unit software can compensate for the inaccuracy and display measurements that account for the inaccuracy (i.e. perform a run-time self-calibration). This may be accomplished by measuring an error pose between the actual and reference tool locations, and applying the inverse of the error pose to subsequent measurements.

Non-NFT Verification of Calibration of Sensor-Mounted Tool

Figure 12A:
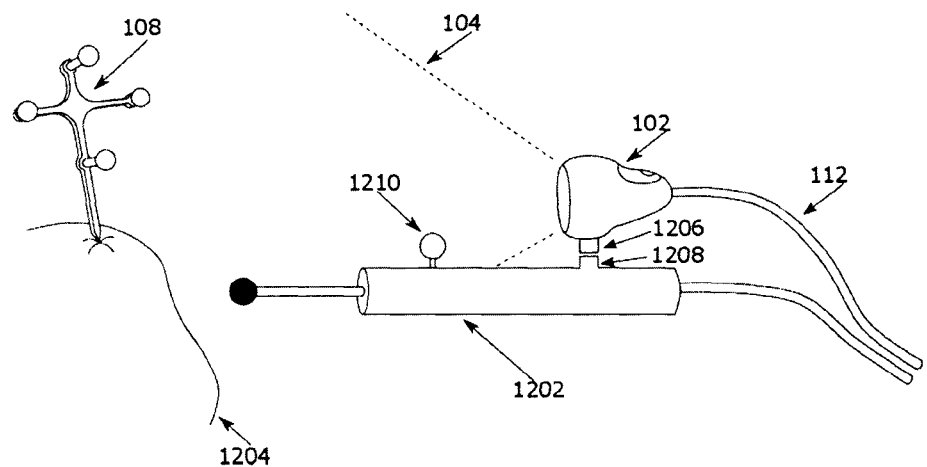
FIG. 12a shows a sensor kinematically coupled to a bone cutting instrument with an optically identifiable marker and a target attached to a patient's body as an example for clarity.

In one embodiment, a non-natural feature may be used to verify the calibration of the positional relationship between a sensor 102 and an object. For example, with reference to FIG. 12a, the object is a haptic/robotic bone cutting tool 1202 (e.g. burring tool). The tool 1202 is configured to cut and/or remove bone 1204 under guidance provided by a relative pose measurement between the sensor 102 and the target 108, when that bone 1204 has a target 108 attached to it. The sensor 102 has a kinematic mount 1206. The tool 1202 has a cooperating kinematic mount 1208 for kinematic coupling to the sensor 102, such that there is a known positional relationship (in up to 6 DOF) between the sensor 102 and the tool 1202. The tool provides an optically trackable feature 1210 that lies within the FOV 104 of the sensor 102. The optically trackable feature 1210 is not a natural feature related to the geometry of the tool 1202; rather, it is a dedicated feature in a known spatial relationship with the position of the end-effector of the tool, and intended to be optically detected by the sensor.

Figure 12B:
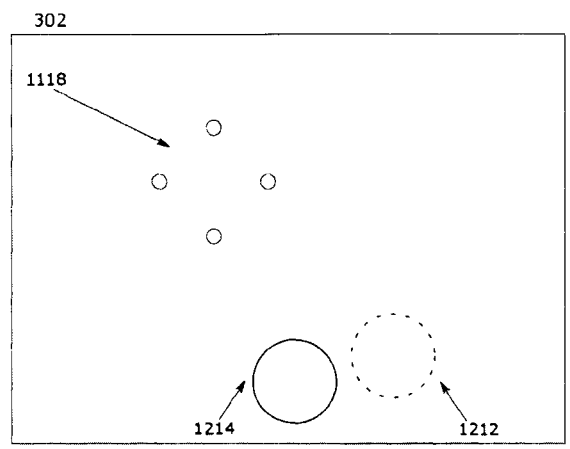
FIG. 12b is a line drawing showing a representative optical sensor image depicting a feature to verify calibration using an optically trackable marker.

Reference is made to FIG. 12b. The optical sensor image shows the optically trackable retro-reflective marker 1210. In the computing unit, the position of the reference marker is known (i.e. the expected position of the marker) based on pre-loaded information. The accuracy of the calibration is verified when the positions of the reference marker and actual marker align/overlap. If not, then the computing unit may notify the user to prevent incorrect therapy from being delivered to the patient. This comparison may be done by the processing unit or via a user assessment relying on a display of the virtual projection of the optically trackable feature superimposed on the actual image of the optically trackable feature as a composite image. Both options may rely on previously-described techniques/methods.

By measuring the position of the marker in the two-dimensional optical sensor image, the system may be tolerant to a compromised, or unknown positional relationship between the end-effector and the sensor; a calibration or compensation may be performed based on the expected position of the marker in the image. It should be noted that multiple markers, or other features visible to the sensor, may be used to detect and/or compensate for a compromised positional relationship between the sensor and the instrument. It should be noted that where robotic actuation is used to assist with delivering guided therapy, verifying the accuracy of the end-effector is critical since the robot is functioning autonomously and the user/surgeon does not relying on human clinical judgment.

Clinical Applications

Figure 13:
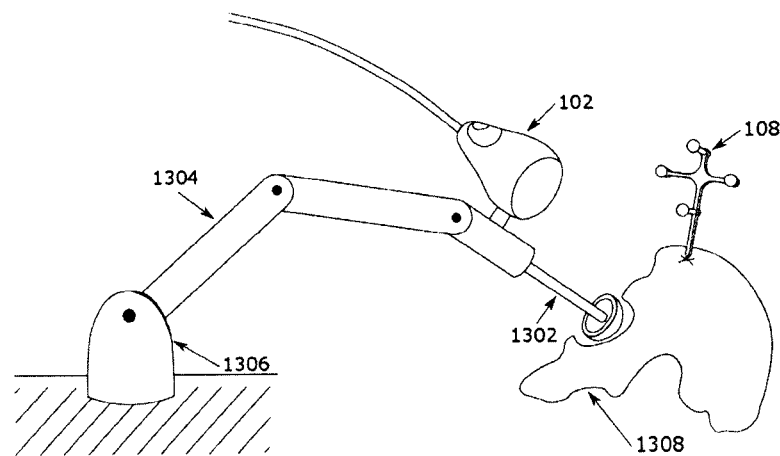
FIG. 13 shows a sensor kinematically coupled to a robotic manipulator and a target attached to a patient's anatomy as an example for clarity.

Those skilled in the art will appreciate how the following applications may benefit from the concepts described herein. In one embodiment, with reference to FIG. 13, the sensor 102 is attached to a tool, which is an end-effector 1302 of a robot manipulator 1304 (e.g. used for haptically guided and/or robotic surgery). The robot manipulator 1304 has a base surface 1306 that is anchored to the ground (i.e. to some reference within a room), or to a patient's anatomy (e.g. to a bone, such as a robotic knee cutting guide). The sensor 102 is kinematically coupled with the end-effector 1302, and the position of the end-effector 1302 with respect to a bone 1308 is tracked in real time using the target 108.

Figure 14:
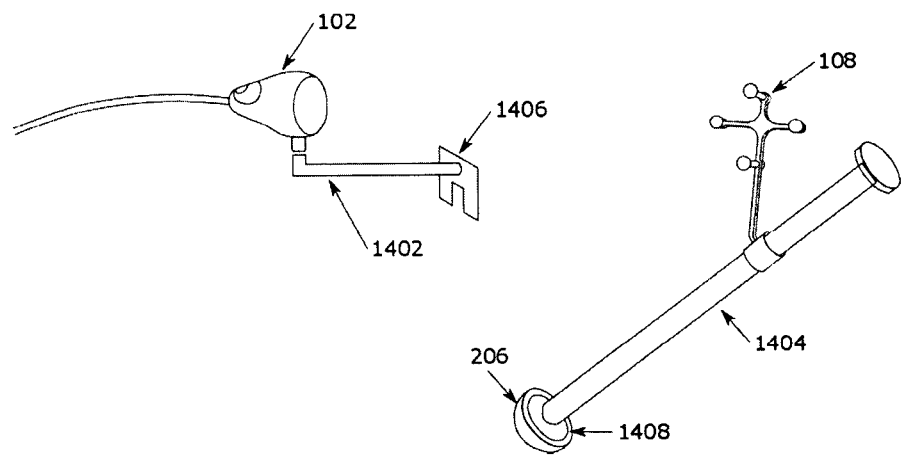
FIG. 14 shows a sensor coupled to a calibration tool for use with an impactor as an example for clarity.

In one embodiment, with reference to FIG. 14, a calibration tool 1402 is kinematically coupled to the sensor 102. The target 108 is coupled to a surgical instrument that needs calibration (e.g. an acetabular cup impactor 202 used in THA). The calibration tool 1402 has features such as, a calibration contact surface 1406 that is configured to mate with the surface of an opening plane 1408 of the acetabular cup 206. When the calibration tool contact surface 1406 is co-planar with the cup plane 1408, the sensor 102 to target 108 pose is captured, and used to compute the calibration of the surgical instrument (i.e. the positional relationship between the target and the plane of the cup).

Figure 15:
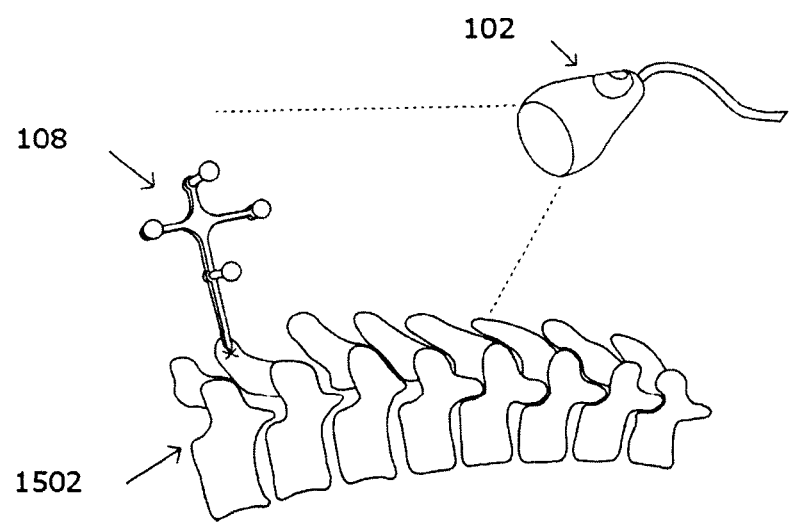
FIG. 15 shows use of a surgical tracking system to register anatomy to a target in accordance with an embodiment.

Natural Feature Scanning+Simultaneous Target Tracking Using Optical Camera for NFS In addition to calibrating a target to a tool by simultaneously tracking targets and natural features, registration of a target to anatomy is also contemplated. By way of example, in FIG. 15, a target 108 is attached to a spine 1502 of a patient who is undergoing a spinal surgical procedure. The sensor 102 is aimed (either manually by the surgeon, or otherwise) at the target 108, but also has several spatial attributes of the anatomy, in this case exposed vertebrae, within its FOV 104. The sensor 102 measures the pose of the target 108, and simultaneously measures the pose of the vertebrae, thus allowing the relative pose between the anatomy (i.e. vertebrae) and the target to be determined. This relative pose is referred to as an anatomical registration.

Figure 16A:
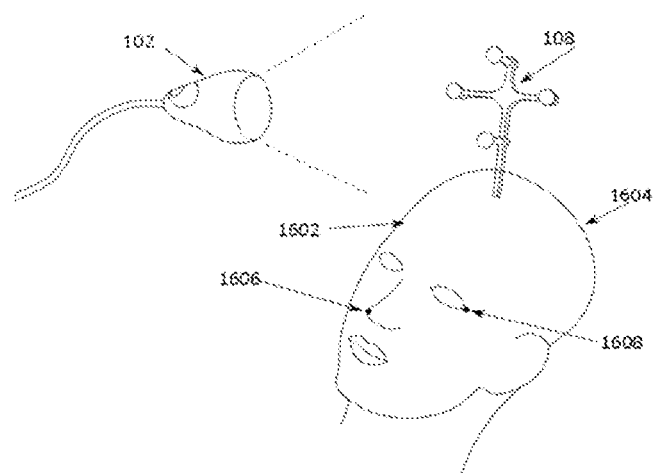
FIG. 16a illustrates a sensor detecting spatial attributes of a face to create a registration to a target, in accordance with an embodiment.
Figure 16B:
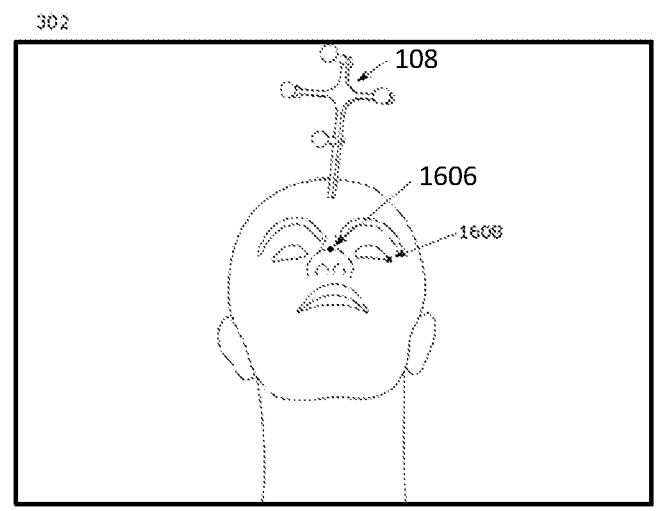
FIG. 16b is a line drawing showing a representative optical sensor image of a sensor viewing spatial attributes of a face, in accordance with an embodiment.

An example in accordance with an embodiment illustrated in FIG. 16a. The target 108 is coupled to a patient's head (invasively or non-invasively). The sensor 102 captures spatial attributes such as, the patient's facial features 1602, as well as the target 108 within its field of view 104, in order to register a relationship between the target 108 and the patient's head 1604. An optical image 302 generated by the sensor 102 with the target 108 and facial features (the tip of the nose 1606 and the corner of the eye 1608, for example) within its field of view is illustrated in FIG. 16b.

Registration of anatomical features (e.g. vertebrae, facial features) or other spatial attributes using an optical sensor may be more challenging than measuring the pose of geometrically well-defined objects such as surgical tools. This is because the anatomical features are less geometrically well-defined. Furthermore, anatomical features may be occluded by soft tissues, blood, etc., making them more difficult to detect using an optical sensor.

Figure 17:
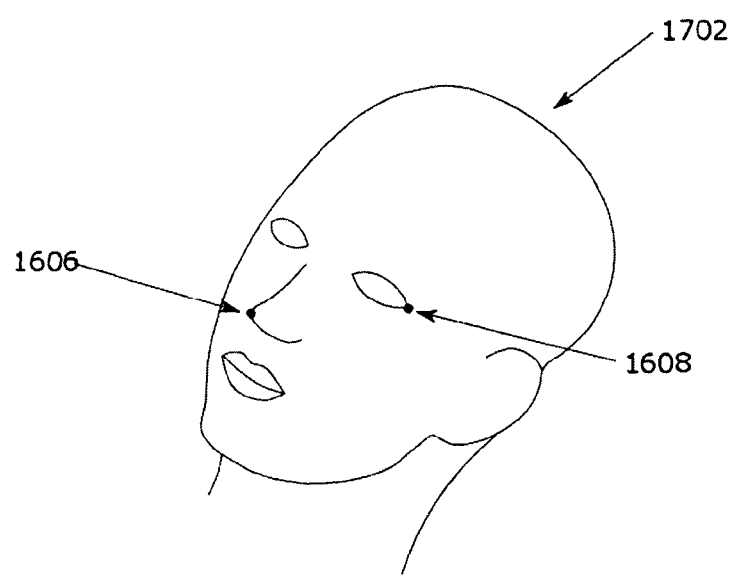
FIG. 17 depicts a 3D scan of a patient's anatomy that can be used in registration.

In one embodiment, the anatomical geometry is known a priori to the computing unit 110 for use in calculating a registration of the anatomical geometry. As illustrated in FIG. 17, the anatomical geometry may be in the form of a pre-operative scan 1702 (e.g. CT or MRI of the anatomy) that is specific to a patient. The known anatomical geometry aids in solving for the relative pose between the anatomy and the target, as it facilitates mapping the optical sensor image of the anatomy to the 3D scan 1702. The computing unit 110 relies on a correspondence between anatomical features in the optical sensor image 302 with corresponding anatomical features in the 3D scan 1702. For example, with reference to FIG. 16a and FIG. 17, corresponding anatomical features (e.g. the tip of the nose 1606, the corner of the eye 1608) may be identified on the 3D scan 1702 and on the optical image 302. The correspondence of points on the optical sensor image 302 and the 3D scan 1702 may be created automatically (i.e. by the computing unit), semi-automatically (i.e. by the computing unit with limited user intervention) or manually (i.e. by the user, for example, identifying corresponding points by clicking on them on a computer screen). Any number of corresponding points may be used to aid in the calculation of the registration. Rather than a 3D scan, a generic 3D model may be used where the 3D model describes the anatomy with sufficient accuracy for the purposes of registration e.g. using a 3D model of a face that is not specific to the face of a patient undergoing surgery.

Figure 18A:
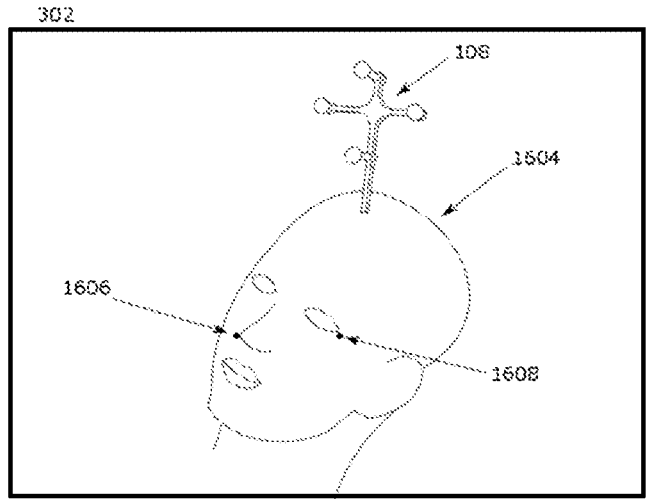
FIG. 18a and FIG. 18b depict line drawings showing representative optical sensor images from two vantage points.
Figure 18B:
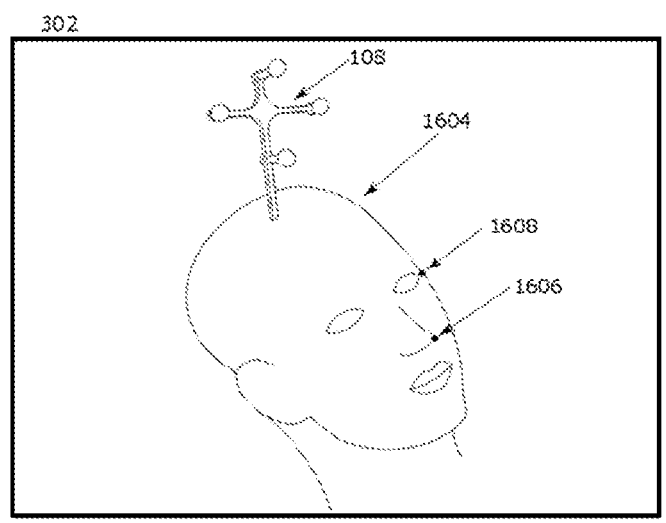

In another embodiment, the anatomical registration may rely on multiple measurements from a plurality of vantage points of the anatomical features and the target. FIG. 18a and FIG. 18b illustrate two optical sensor images from two vantage points. Measurements from a plurality of vantage points provide more geometrical information content to register the anatomy with high accuracy. It is particularly advantageous for the measurements from different vantage points to include the target in the optical sensor image since the pose of the target may be measured with high accuracy. Knowledge of the various vantage points (e.g. knowledge that two vantage points are separated by a particular distance or angle) when detecting anatomical features that are part of the anatomical registration eliminates unknown variables when the computing unit solves the pose (i.e. the "extrinsic parameters" between sensor vantage points is known, and does not need to be solved for). A person skilled in the art will appreciate that having known extrinsic parameters for the camera improves registration accuracy.

A user may receive feedback from the computing unit e.g. through a display unit, providing instructions to the user to capture multiple measurements from a variety of vantage points. For example, the instructions may direct a user to capture a certain number of optical sensor images containing the target and the anatomy to be registered from prescribed viewing angles and vantage points. The images may be measured discretely or continuously (i.e. a continuous collection of a plurality of views).

In another embodiment, where the system is collecting a plurality of images of the target and anatomy, the system is tolerant of not being able to identify any number of markers (i.e. identifiable features on the target) for a subset of the images (e.g. because the markers are occluded, outside the sensor field of view, etc.). This is achieved by initially tracking both the target and the anatomical features, and when a subset of the markers are not available, tracking only based on the available target markers (if any) and the available anatomical features.

Using Other Scanning Modalities for NFS

In addition to identifying features (e.g. anatomical features) in an optical sensor image for anatomical registration, it may be advantageous for the sensor to measure the depth of objects within its field of view. A depth image from a depth image sensor with a field of view that overlaps with the field of view of the optical sensor may be advantageous in calculating the pose of an object based on its natural features. In one embodiment, a depth image is provided to the computing unit by the sensor via a depth image sensor. Whereas an optical sensor image is a measurement of light intensity of a scene on a plurality of pixels, a depth image is a measurement of distance of objects in a scene to the depth image sensor on a plurality of pixels. It is advantageous for the depth image and optical sensor image to be overlapping when capturing images of an object, since the optical and depth measurements can be combined to aid in measuring pose of objects. Furthermore, depth images of an object may be captured while tracking a target affixed to the object, and used to reconstruct the 3D surface profile of the object.

The optical image and the depth image are preferably related to a common coordinate frame (aka "co-registered"); such that both optical and depth measurements may be used to calculate the relative pose between a target (coupled to the anatomy) and the anatomy itself. The coordinate frames of the optical sensor and depth sensor may be co-registered by design, through factory calibration, etc. with a fixed and known positional relationship between the optical sensor and the depth sensor.

In one embodiment, the depth image sensor is a time-of-flight imager. The time-of-flight imager produces an optical sensor image and a depth image using the same optical components (for e.g. the imager chip). This is advantageous as the depth and optical images overlap by default. The optical and depth images are inherently co-registered since they are generated by the same imager chip.

In one embodiment, the depth image is generated by the optical sensor in combination with modulated illumination. In its simplest form, a depth image may be generated by applying a constant illumination to a scene, and measuring brightness of content within the scene; the brightness of the content is correlated to proximity (i.e. depth). Alternatively, the illumination may be modulated temporally (e.g. a sinusoidal wave of illumination intensity) or spatially (e.g. illumination sequentially firing from multiple points on the sensor). The illumination modulation may be used to enhance the ability to accurately generate a depth image. Using modulated illumination is advantageous since it relies on the optical sensor to obtain depth information and this configuration is inherently co-registered since a single sensor is being used.

In one embodiment, the sensor comprises components that project structured light onto the object being viewed by the optical sensor. The structured light is reflected back to the optical sensor and provided to the computing unit. The computing unit may receive the optical sensor image, and generate a depth image of a scene within which lies the object, based on how the structured light appears in the optical sensor image. This configuration is advantageous because it relies on the optical sensor to measure/estimate depth; also, this configuration is inherently co-registered. This configuration requires that the components that project structured light be co-registered to the optical sensor.

In one embodiment, a laser scanner is coupled to the sensor, and configured to generate a depth image. Where the sensor is configured to measure the pose of a target (coupled to an object), and the laser scanner is configured to generate a depth image of the object, and where the laser scanner and the sensor have a co-registered relationship, the depth image of the object (associated with the pose of the object) may be known relative to the target. The laser scanner may be a separate device that is able to kinematically mate with the sensor in a known co-registered position. The laser scanner may then be used during anatomical registration, and removed otherwise, so as not to increase the size/bulkiness of the sensor.

In the previously described embodiments, it may be advantageous to further utilize multiple views of the target and the anatomy to be registered, from different vantage points. Depth image sensors may be susceptible to noise and inaccuracies; utilizing multiple views may increase the accuracy of the reconstructed depth map. Similar to a previously-mentioned embodiment, having known extrinsic parameters between two optical/depth measurements of a scene may greatly improve the accuracy, robustness and reduce the computational burden of pose measurement of the anatomy.

In the previously described embodiments, it may be advantageous to utilize a 3D scan of the anatomy (e.g. CT or MRI scan) when solving for relative pose between the target and the anatomy. Point correspondence may be performed between the various locations on the 3D scan and the corresponding locations on the optical sensor image and/or the depth image. A generic 3D model of the anatomy may also be used, rather than a specific 3D scan of the anatomy.

In one embodiment, a sensor is attached to a calibration probe of a known geometry (e.g. known length). The calibration probe is intended to calibrate the depth image sensor. When the calibration probe is brought into contact with an object, the object is at a known distance (depth) from the sensor. A depth image is measured at this time, and the depth image is calibrated based on the known depth. Furthermore, the calibration probe may be optically trackable via its natural features to facilitate calibration between the optical sensor and the depth sensor. The computing unit in communication with the sensor may perform a calibration or verification based on the optical and depth images.

The above embodiments may be useful in a variety of surgical applications, including the previously-presented cranial application, wherein it is desirable to localize relative to a patient's head. Other applications are contemplated, such as Total Hip Arthroplasty. For example, the anatomy may be an acetabulum of a pelvis. It may be desirable to know the registration between a target, attached to the pelvis, and the acetabulum. Alternatively, it may be desirable simply to know the surface profile of a reamed acetabulum, for example, to check whether the acetabulum was reamed eccentrically. Should eccentricity (or other defects which lead to poor cup seating) be detected, corrective action may be taken by the surgeon prior to implantation of the cup. An advantage of this approach is to avoid removing and/or repositioning the cup. Cup removal may result in scrapping the original cup (since further reaming is required, increasing the size of the required cup).

Figure 19:
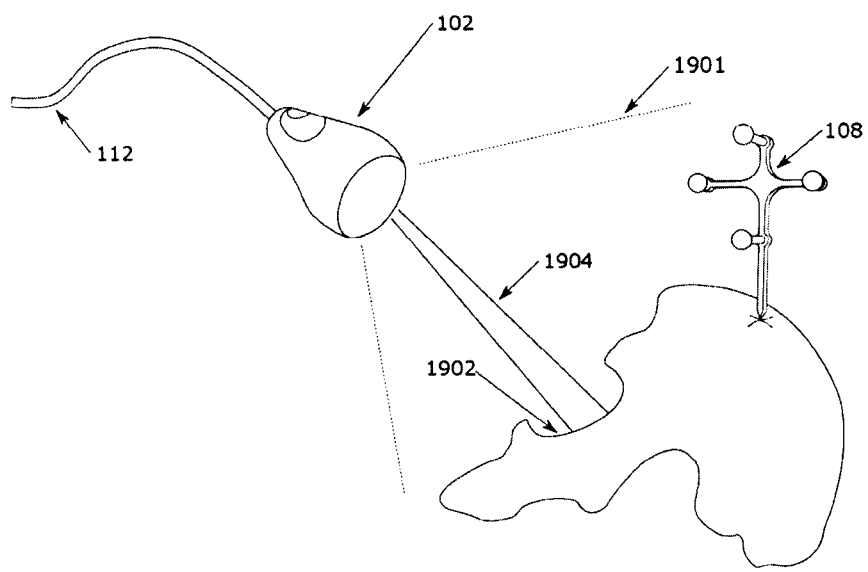
FIG. 19 shows a system with a target on a pelvis, and a depth sensor scanning an acetabular surface.

FIG. 19 depicts a sensor 102, comprising an optical sensor and depth sensor, with an overlapping field of view 1901 within which lies a target 108 attached to a pelvis and an exposed acetabulum. The sensor 102 scans the surface of the acetabulum 1902 with light 1904 (e.g. structured light). The sensor 102 connects to a computing unit 110 that can perform further calculations to determine registration of the acetabulum to the target.

Figure 20:
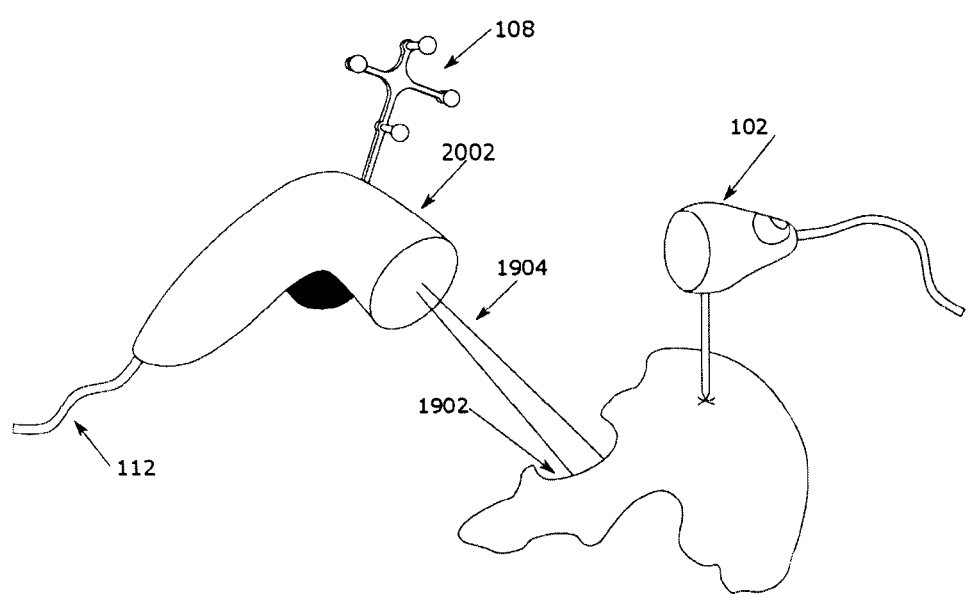
FIG. 20 shows a system with a target on the depth sensor scanning an acetabular surface, and an optical sensor on a pelvis.

An alternative configuration is illustrated in FIG. 20, wherein the sensor 102 is mounted to the anatomy (the pelvis), and the target 108 is mounted onto a surface scanner 2002 (comprising a depth sensor). In this configuration, the target and the depth sensor have a co-registered relationship as the optical sensor can track the pose of the target that is attached to the depth sensor. Furthermore, the depth sensor and the optical sensor both communicate with the computing unit 110.

Hardware to Support Tracking Targets and Natural Features

Figure 21:
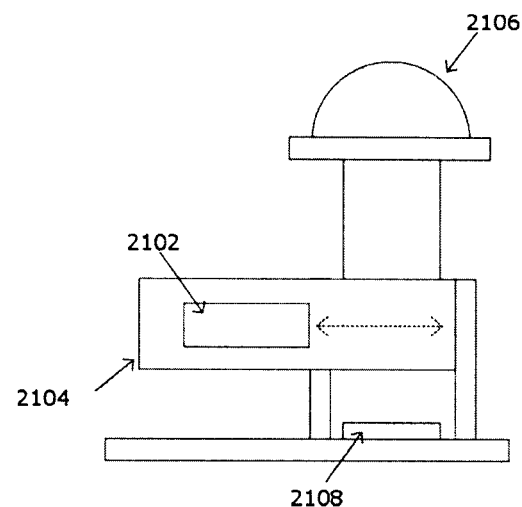
FIG. 21 shows a hardware configuration of a sensor with a switchable optical filter for use in different spectra.
Figure 22:
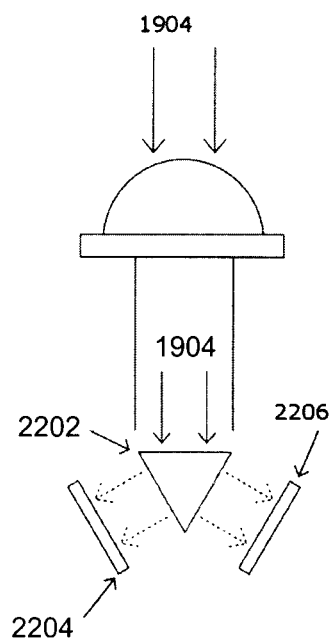
FIG. 22 shows a hardware configuration of an optical sensor using two imagers.

A camera may be used to track natural features. The camera's spectral range (i.e. the range of light frequencies to which it is sensitive) must be able to detect natural features. Typically, visible spectra are good for this purpose; however, with appropriate illuminating components, infra-red or near infra-red spectra may also be suitable. If markers on the target are accurately and positively identifiable in the same spectra as the natural features, then a fixed camera (including the lens, optical filtering, imager, and illuminating components) may be utilized.

Where different spectra are used for tracking of natural features and tracking of targets, a switchable optical filter may be utilized within the sensor. For example, in FIG. 21, an optical filter 2102 is electronically switchable via a solenoid assembly 2104 to switch between unfiltered and filtered light passing through to a lens 2106 on to an imager 2108. Rather than a solenoid, a motor with a filter wheel may be used, and synchronized with the exposure cycles of the camera. For example, alternating image frames may be synchronized such that they are with/without filtering. That is, for a 40 frames-per-second camera, it is possible to obtain two 20 frames-per-second video feeds in two different spectra.

Where different spectra are used for tracking of natural features and tracking of targets, a spectrum splitter may be utilized within the camera. As illustrated in FIG. 22, a prism 2202 may be used for this purpose. In this figure, two imagers 2204, 2206 are depicted, each dedicated to a different spectral response of incoming light. There is no limitation to dividing the spectrum into two; more divisions of the spectra may be created as necessary.

Similarly, where different spectra are used for tracking of natural features and tracking of targets, a second optical sensor may be integrated within the sensor to detect light in the other spectrum (i.e. the sensor is comprised of two optical sensors operating in two different spectra). In this case, both cameras must be related to a common coordinate frame, or co-registered (e.g. through manufacturing, factory calibration, etc.).

In embodiments where the sensor utilizes structured light for depth and/or pose measurement, the sensor may incorporate a structured light projector that projects structured light detectable by the optical sensor into the optical sensor's field of view. In embodiments utilizing modulated illumination for generation of depth images, the sensor may incorporate the necessary digital and/or analog circuits to implement and/or control the modulation of illumination being projected into the optical sensor's field of view.

Reference is now made to FIG. 23. There is disclosed a computer-implemented method 2300, comprising: at step 2302, a computing unit in communication with a sensor comprising an optical sensor, calculating a pose of a target in up to 6DOF using optical measurements generated by the sensor. At step 2304, the computing unit determines an expected location of the effector of the tool based on pre-loaded information of the tool, the sensor being attached to the tool at a known positional relationship. Step 2306 involves determining a location of the effector of the tool based on features detected from an optical sensor image generated by the optical sensor. At step 2308, a difference is calculated between the location and expected location of the effector of the tool, leading to the generation of a confidence metric using the difference at step 2310.

Figure 24:
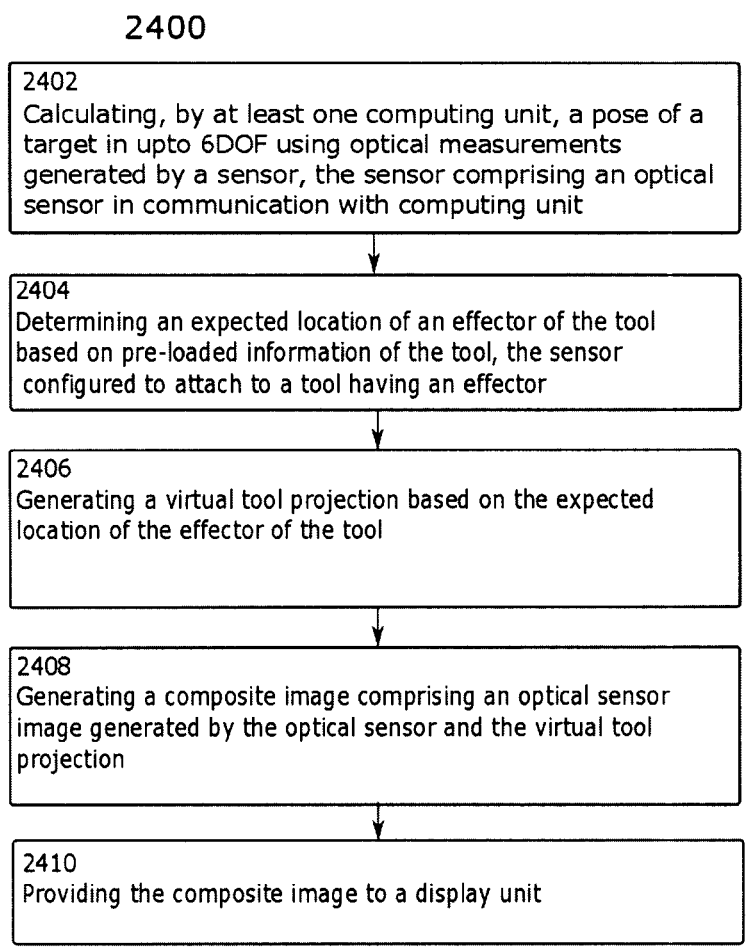

Reference is now made to FIG. 24. There is disclosed a computer-implemented method 2400, comprising: at step 2402, a computing unit in communication with a sensor comprising an optical sensor, calculating a pose of a target in up to 6DOF using optical measurements generated by the sensor. At step 2404, the computing unit determines an expected location of the effector of the tool based on pre-loaded information of the tool, the sensor being attached to the tool at a known positional relationship. Step 2406 involves generating a virtual tool projection based on the expected location of the effector of the tool, and at step 2408, a composite image is generated by the computing unit comprising an optical sensor image generated by the optical sensor and the virtual tool projection, for display on a display unit.

Accordingly, it is to be understood that this subject matter is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible.

What is claimed is:

1. A system comprising:
   a sensor comprising an optical sensor, the optical sensor configured to generate an optical sensor image of a tool and a target attached to the tool at a known positional relationship, the tool having an effector with the tool lying within a field of view of the optical sensor, the sensor configured to use the optical sensor image of the tool and to generate optical measurements of the target, wherein the target lying in the field of view of the optical sensor and providing positional information for the tool; and
   a computing unit in communication with the sensor, the computing unit configured to:
   calculate a pose of the target in up to six degrees of freedom using the optical measurements;
   determine an expected location of the effector of the tool based on first pre-loaded information of the tool comprising a location for the effector on the tool responsive to a known position of the target on the tool;
   determine a feature tracked location of the effector of the tool based on second pre-loaded information of the tool comprising feature information describing features of the tool for detection; and the features of the tool as detected from the optical sensor image of the tool;
   wherein the expected location and the feature tracked location comprise two real-time location measures of the effector of the tool when located at a same location, the two measures determined in two different manners;
   calculate a difference between the feature tracked location and expected location of the effector of the tool;
   generate a confidence metric using the difference;
   and provide positional measurements of the effector of the tool with respect to the optical sensor, the positional measurements being provided with the confidence metric and being responsive to the pose of the target.

2. The system of claim 1, wherein the optical sensor is attached to an object which is different from the tool.

3. The system of claim 2, wherein the object is a patient.

4. The system of claim 1, further configured to provide the confidence metric to a display unit to display in one of a numerical or graphical format.

5. The system of claim 1, wherein the computing unit is further configured to prevent surgical navigation using the positional measurements when the confidence metric is outside of a tolerance range.

6. The system of claim 1, wherein the computing unit determines the feature tracked location of the effector of the tool by calculating a pose of the effector of the tool and further determines the expected location of the effector of the tool by calculating an expected pose of the effector of the tool.

7. The system of claim 1, wherein the optical sensor image comprises a two-dimensional optical sensor image and the computing unit determines the feature tracked location of the effector of the tool by calculating a position of the effector of the tool within a coordinate frame of the two-dimensional optical sensor image and further determines the expected location of the effector of the tool by calculating an expected position of the effector of the tool within the coordinate frame of the two-dimensional optical sensor image.

8. A system to provide surgical navigation of an effector of a tool with respect to a pose of a target comprising:
   a sensor comprising an optical sensor including a camera to generate an optical sensor image of a tool and a target attached to the tool at a known positional relationship, the tool having an effector with the tool lying within a field of view of the optical sensor for inclusion in optical sensor images by the camera, the sensor configured to use the optical sensor image of the tool and to generate optical measurements of the target, wherein the target lying in the field of view of the optical sensor and providing positional information for the tool is attached, the object being different from the tool; and
   a computing unit in communication with the sensor, the computing unit configured to, when the optical sensor is attached to the tool:
   calculate a pose of the target in up to six degrees of freedom using the optical measurements;
   determine an expected location of the tool based on first pre-loaded information of the tool comprising a location for the effector on the tool responsive to a known position of the target on the tool;
   generate a virtual tool projection based on the expected location of the tool;
   generate a composite image comprising the optical sensor image and the virtual tool projection; and
   provide the composite image to a display unit.

9. The system of claim 8 further comprising a display unit to display the composite image.

10. The system of claim 8, wherein the computing unit is configured to generate the composite image further comprising virtual error bounds.

11. The system of claim 8, wherein the optical sensor is attached to an object and wherein the optical sensor is configured to provide positional information of the target and wherein the computing unit is configured to provide surgical navigation with respect to the optical sensor.

12. The system of claim 11, wherein the optical sensor is configured to attach to an anatomy of a patient.

13. The system of claim 8, wherein the target further comprises a kinematic mount for attachment to a cooperating kinematic mount on the tool, and the pre-loaded information comprises a first positional relationship between the target and the kinematic mount of the sensor, and a second positional relationship between the cooperating kinematic mount and the tool.

14. The system of claim 8, wherein an optically detectable marker is attached to the tool, and the computing unit is further configured to determine the expected location of the tool based on the pre-loaded information of the tool, the pre-loaded information comprising a spatial relationship between the target and the optically detectable marker, and the virtual tool projection comprising a virtual projection of the optically detectable marker.

15. A system comprising:
a sensor comprising an optical sensor, the optical sensor configured to generate an optical sensor image of a robot and of a target each lying in a field of view of the optical sensor, wherein:
one of the sensor and the target is configured to attach to the robot at a known positional relationship and the other of the sensor and the tool is configured to attach to an object that is different from the robot, the robot comprising an effector,
the target providing positional information for one of the robot and the object to which the target is attached, and
the sensor is configured to use the optical sensor image of the robot and to generate optical measurements of the target; and
a computing unit in communication with the sensor, the computing unit configured to:
calculate a pose for the target in up to six degrees of freedom using the optical measurements, when the target is attached to the one of the robot and the object;
determine an expected location of the effector of the robot based on first pre-loaded information of the robot comprising a location for the effector on the robot responsive to a known position of the one of the sensor and target when attached to the robot;
determine a feature tracked location of the effector of the robot based on second pre-loaded information of the tool comprising feature information describing features of the robot for detection; and the features of the robot as detected from the optical sensor image of the tool;
wherein the expected location and the feature tracked location comprise two real-time location measures of the effector of the robot when located at a same location, the two measures determined in two different manners;
calculate a difference between the feature tracked location and expected location of the effector of the robot;
responsive to the difference as calculated, provide a signal to control a robotic system operating the robot.

16. The system of claim 15, wherein the signal indicates to the robotic system to stop proceeding with a planned trajectory for the effector.

17. The system of claim 15, wherein the computing unit is configured to calculate a confidence metric responsive to the difference and providing the signal responsive to the confidence metric.

18. The system of claim 15, wherein the computing unit is further configured to provide positional measurements of the effector.

* * * * *